(12) United States Patent
Stephanopoulos et al.

(10) Patent No.: US 7,739,055 B2
(45) Date of Patent: Jun. 15, 2010

(54) METHODS AND SYSTEMS FOR GENERATING AND EVALUATING PEPTIDES

(75) Inventors: Gregory Stephanopoulos, Winchester, MA (US); Kyle Jensen, Berkeley, CA (US); Christopher Loose, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 108 days.

(21) Appl. No.: 11/561,266

(22) Filed: Nov. 17, 2006

(65) Prior Publication Data

US 2007/0197773 A1    Aug. 23, 2007

Related U.S. Application Data

(60) Provisional application No. 60/737,654, filed on Nov. 17, 2005.

(51) Int. Cl.
*G06F 19/00*    (2006.01)
(52) U.S. Cl. .......................... 702/19; 530/300; 530/328
(58) Field of Classification Search ........................ None
See application file for complete search history.

(56) References Cited

U.S. PATENT DOCUMENTS

| | | | |
|---|---|---|---|
| 4,098,728 A | 7/1978 | Rosenblatt | |
| 4,211,227 A | 7/1980 | Anderson et al. | |
| 4,636,208 A | 1/1987 | Rath | |
| 5,180,375 A | 1/1993 | Feibus | |
| 6,031,074 A | 2/2000 | Saxinger | |
| 6,188,965 B1 | 2/2001 | Mayo et al. | |
| 6,269,312 B1 | 7/2001 | Mayo et al. | |
| 6,642,353 B1 | 11/2003 | McConnell et al. | |
| 6,708,120 B1 | 3/2004 | Mayo et al. | |
| 6,711,879 B2 | 3/2004 | Korteweg et al. | |
| 2003/0130827 A1 | 7/2003 | Bentzien et al. | |

(Continued)

FOREIGN PATENT DOCUMENTS

| WO | WO 94/25484 | 11/1994 |
|---|---|---|
| WO | WO 00/09553 | 2/2000 |

(Continued)

OTHER PUBLICATIONS

Brazma et al. Pattern Discovery in Biosequences. Lecture Notes in Computer Science. vol. 1433 Springer Berlin / Heidelberg, 1998.*

(Continued)

*Primary Examiner*—Michael Borin
(74) *Attorney, Agent, or Firm*—Pabst Patent Group LLP

(57) ABSTRACT

Methods to create databases of peptides having a desirable property, such as antimicrobial activity, involving analyzing a database of known peptides for a pattern statistically associated with the desirable property are described herein, The set of sequences being analyzed may include sequences of a desired length containing all or substantially all combinations of amino acids that conform to at least one of the set of patterns. Once the database is identified, the database may be processed in a pattern recognition procedure that identifies a set of patterns that may be representative of a peptide having the desirable property. A set of newly generated peptides sequences may then be processed to score these new sequences against the identified patterns to correlate the patterns to the sequences and determine a degree of association or similarity between one or more of the new sequences and the set of identified patterns.

3 Claims, 3 Drawing Sheets

U.S. PATENT DOCUMENTS

2004/0043430 A1   3/2004  Dahiyat et al.
2008/0133142 A1*  6/2008  Rigoutsos et al. ............. 702/19

OTHER PUBLICATIONS

Rigoutsos et al. Proteins: Structure, Function, and Bioinformatics. vol. 37 Issue 2, pp. 264-277, 1999.*

Wang et al. APD: the Antimicrobial Peptide Database. Nucleic Acids Research, 2004, vol. 32, D590-D592.*

Altschul, et al., "Basic local alignment search tool", *J. Mol. Biol.*, 215(3):403-10 (1990).

Anonymous, "IUPAC-IUB Commission on Biochemical Nomenclature Symbols for Amino-Acid Derivatives and Peptides. Recommendations", *Biochemistry*, 11(9):1726-32 (1971).

Bailey and Elkan, "Fitting a mixture model by expectation maximization to discover motifs in biopolymers", *Proc. Int. Conf. Intell. Syst. Mol. Biol.*, 2:28-36 (1994).

Bairoch and Apweiler, "The Swiss-Prot protein sequence database and its supplement TrEMBL in 2000", *Nucleic Acids Res.*, 28(1):45-8 (2000).

Bolon and Mayo, "Enzyme-like proteins by computational design", *Proc. Natl. Acad. Sci. U.S.A.*, 98(25):14274-9 (2001).

Boman, "Antibacterial peptides: basic facts and emerging concepts", *J. Intern. Med.*, 254(3):197-215 (2003).

Chen, et al., "RGD-Tachyplesin inhibits tumor growth", *Cancer Res.*, 61(6):2434-8 (2001).

Chomsky, "Three models for the description of language", *IRE Transactions on Information Theory*, IT-2(3), 113-124 (1956).

Dahiyat, et al., "De novo protein design: fully automated sequence selection", *Science*, 278(5335):82-7 (1997).

Devereux, et al., "A comprehensive set of sequence analysis programs for the VAX", *Nucleic Acids Res.*, 12(1 Pt 1):387-95 (1984).

Ellerby, et al., "Anti-cancer activity of targeted pro-apoptotic peptides", *Nat. Med.*, 5(9):1032-8 (1999).

Epand and Vogel, "Diversity of antimicrobial peptides and their mechanisms of action", *Biochim. Biophys. Acta.*, 1462(1-2):11-28 (1999).

Ge, et al., "In vitro antibacterial properties of pexiganan, an analog of magainin", *Antimicrob. Agents Chemother.*, 43(4):782-8 (1999).

Giangaspero, et al., "Amphipathic alpha helical antimicrobial peptides", *Eur. J. Biochem.*, 268(21):5589-600 (2001).

Han and Kang, "Sequence analysis and membrane partitioning energies of alpha-helical antimicrobial peptides", *Bioinformatics*, 20(6):970-3 (2004).

Hancock and Patrzykat, "Clinical development of cationic antimicrobial peptides: from natural to novel antibiotics", *Curr. Drug Targets Infect. Disord.*, 2(1):79-83 (2002).

Henikoff and Henikoff, "Amino acid substitution matrices from protein blocks", *Proc. Natl. Acad. Sci. U.S.A.*, 89(22):10915-9 (1992).

Hruby, et al., "Design of peptides, proteins, and peptidomimetics in chi space", *Biopolymers*, 43(3):219-66 (1997).

Joseph-McCarthy, "Computational approaches to structure-based ligand design", *Pharmacol. Ther.*, 84(2):179-91 (1999).

Kamtekar, et al., "Protein design by binary patterning of polar and nonpolar amino acids", *Science*, 262(5140):1680-1685 (1993).

Kim, et al., "In vitro activities of native and designed peptide antibiotics against drug sensitive and resistant tumor cell lines", *Peptides*, 24(7):945-53 (2003).

Kimbrell and Beutler, "The evolution and genetics of innate immunity", *Nat. Rev. Genet.*, 2(4):256-667 (2001).

Koehl and Levitt, "De novo protein design. II. Plasticity in sequence space", *J. Mol. Biol.*, 293(5):1183-93 (1999).

Kopple, "Peptides and Amino Acids", W. A. Benjamin Inc., pp. 2 and 33, Paub: New York and Amsterdam, 1966.

Kraemer-Pecore, et al., "Computational protein design", *Curr. Opin. Chem. Biol.*, 5(6):690-5 (2001).

Lawrence, et al., "Detecting subtle sequence signals: a Gibbs sampling strategy for multiple alignment", *Science*, 262(5131):208-14 (1993).

Looger, et al., "Computational design of receptor and sensor proteins with novel functions", *Nature*, 423(6936):185-90 (2003).

Maizel and Lenk, "Enhanced graphic matrix analysis of nucleic acid and protein sequences", *Proc. Natl. Acad. Sci. U.S.A.*, 78(12):7665-9 (1981).

Moerman, et al., "Antibacterial and antifungal properties of alpha-helical, cationic peptides in the venom of scorpions from southern Africa", *Eur. J. Biochem.*, 269(19):4799-810 (2002).

Nikiforovich, "Computational molecular modeling in peptide drug design", *Int. J. Pept. Protein Res.*, 44(6):513-31 (1994).

Putsep, "Deficiency of antibacterial peptides in patients with morbus Kostmann: an observation study", *Lancet*, 360(9340):1144-9 (2002).

Regan and Degrado, "Characterization of a helical protein designed from first principles", *Science*, 241(4868):976-8 (1988).

Rice, et al., "EMBOSS: the European Molecular Biology Open Software SuiteEMBOSS: the European Molecular Biology Open Software Suite", *Trends Genet.*, 16(6):276-7 (2000).

Rigoutsos and Floratos, "Combinatorial pattern discovery in biological sequences: The Teiresias algorithm", *Bioinformatics*, 14(1):55-67 (1998).

Rigoutsos, et al., "Dictionary building via unsupervised hierarchical motif discovery in the sequence space of natural proteins", *Proteins*, 37(2):264-77 (1999).

Rigoutsos, "The emergence of pattern discovery techniques in computational biology", *Metab. Eng.*, 2(3):159-77 (2000).

Rolff and Siva-Jothy, "Invertebrate ecological immunology", *Science*, 301(5632):472-5 (2003).

Salzman, et al., "Protection against enteric salmonellosis in transgenic mice expressing a human intestinal defensin", *Nature*, 422(6931):522-6 (2003).

Schittek, et al., "Dermcidin: a novel human antibiotic peptide secreted by sweat glands", *Nat. Immunol.*, 2(12):1133-7 (2001).

Schneider, et al., "Peptide design by artificial neural networks and computer-based evolutionary search", *Proc. Natl. Acad. Sci. U.S.A.*, 95(21):12179-84 (1998).

Searls, "Artificial intelligence and molecular biology", (L. Hunter, ed.), pp. 47-120, AAAI Press, 1992.

Searls, "The language of genes", *Nature*, 420(6912):211-7 (2002).

Shimaoka, et al., "Computational design of an integrin I domain stabilized in the open high affinity conformation", *Nat. Struct. Biol.*, 7(8):674-8 (2000).

Simmaco, et al., "Antimicrobial peptides from amphibian skin: what do they tell us?", *Biopolymers*, 47(6):435-50 (1998).

Simmaco, et al., "Antimicrobial peptides from skin secretions of *Rana esculenta*. Molecular cloning of cDNAs encoding esculentin and brevinins and isolation of new active peptides", *J. Biol. Chem.*, 269(16):11956-61 (1994).

Strom, et al., "The pharmacophore of short cationic antibacterial peptides", *J. Med. Chem.*, 46(9):1567-70 (2003).

Swope, "Modern computational techniques", IBM Systems Journal, 40(2) (2001).

Tiozzo, et al., "Wide-spectrum antibiotic activity of synthetic, amphipathic peptides", *Biochem. Biophys. Res. Commun.*, 249(1):202-6 (1998).

Tossi and Sandri, "Molecular diversity in gene-encoded, cationic antimicrobial polypeptides", *Curr. Pharm. Des.*, 8(9):743-61 (2002).

Tossi, et al., "Amphipathic, alpha-helical antimicrobial peptides", *Biopolymers*, 55(1):4-30 (2000).

Wang and Wang, "APD: the Antimicrobial Peptide Database", Nucleic Acids Res., 32(Database issue):D590-2 (2004).

Wilson, et al., "Regulation of intestinal alpha-defensin activation by the metalloproteinase matrilysin in innate host defense", *Science*, 286(5437):113-7 (1999).

Zeng and Treutlein, "A method for computational combinatorial peptide design of inhibitors of Ras protein", *Protein Eng.*, 12(6):457-68 (1999).

Zhang, et al., "Contribution of human alpha-defensin 1, 2, and 3 to the anti-HIV-1 activity of CD8 antiviral factor", *Science*, 298(5595):995-1000 (2002).

* cited by examiner grammar 1: T[L/I/G][T/I/P]-L-L-[T/A/S/T]-[I/S/T]-L-L-[L/G] (SEQ. ID No:6)

query: MKSTGPLLSALLLAVTAGGDP (SEQ. ID No:108)

grammar 2: [A/F/T]-L-[I/L]-L-A-[I/F/M/V/A/A]-[S/M/A/A/T]-[G/G/A/D]-[P/G/S/Q] (SEQ. ID No:7)

B

SEQUENCE LISTING

```
<160> NUMBER OF SEQ ID NOS: 111

<210> SEQ ID NO 1
<211> LENGTH: 21
<212> TYPE: PRT
<213> ORGANISM: Artificial
<220> FEATURE:
<223> OTHER INFORMATION: Exemplary grammer

<400> SEQUENCE: 1

Ile Val Leu Lys Thr Glu Gly Asp Leu Val Gly Ala Lys Ala Glu Leu
1               5                   10                  15

Asn His Gly Ala Lys
            20

<210> SEQ ID NO 2
<211> LENGTH: 12
<212> TYPE: PRT
<213> ORGANISM: Insect
```

```
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: misc_feature
<222> LOCATION: (10)..(11)
<223> OTHER INFORMATION: Xaa can be any naturally occurring amino acid

<400> SEQUENCE: 2

Gln Xaa Glu Ala Gly Xaa Leu Xaa Lys Xaa Xaa Lys
 1               5                  10

<210> SEQ ID NO 3
<211> LENGTH: 23
<212> TYPE: PRT
<213> ORGANISM: Artificial
<220> FEATURE:
<223> OTHER INFORMATION: AmP Grammer

<400> SEQUENCE: 3

Ile Val Leu Lys Thr Glu Gly Asp Lys Val Gly Ala Lys Ala Glu Leu
 1               5                  10                  15

Asn His Val Ala Gly Ala Lys
             20

<210> SEQ ID NO 4
<211> LENGTH: 10
<212> TYPE: PRT
<213> ORGANISM: Frog

<400> SEQUENCE: 4

Pro Lys Ile Phe Cys Lys Ile Thr Arg Lys
 1               5                  10

<210> SEQ ID NO 5
<211> LENGTH: 25
<212> TYPE: PRT
<213> ORGANISM: Artificial
<220> FEATURE:
<223> OTHER INFORMATION: Grammer sequence

<400> SEQUENCE: 5

Pro Lys Ala Tyr Ser Ile Leu Asn Phe Gly Ile Cys Lys Pro Ser Ala
 1               5                  10                  15

Ile Val Thr Ser Arg Lys Cys Lys Arg
             20                  25

<210> SEQ ID NO 6
<211> LENGTH: 18
<212> TYPE: PRT
<213> ORGANISM: Artificial
<220> FEATURE:
<223> OTHER INFORMATION: Grammer 1 sequence

<400> SEQUENCE: 6

Thr Leu Gly Thr Ile Pro Leu Leu Thr Ile Ser Pro Ala Thr Leu Leu
 1               5                  10                  15

Leu Gly
```

```
<210> SEQ ID NO 7
<211> LENGTH: 23
<212> TYPE: PRT
<213> ORGANISM: Artificial
<220> FEATURE:
<223> OTHER INFORMATION: Grammer 2 Sequence

<400> SEQUENCE: 7

Ala Phe Thr Leu Ile Leu Leu Ala Ile Val Ser Phe Ala Thr Val Ala
1               5                   10                  15

Gly Ala Asp Pro Gly Ser Gln
            20

<210> SEQ ID NO 8
<211> LENGTH: 31
<212> TYPE: PRT
<213> ORGANISM: Artificial
<220> FEATURE:
<223> OTHER INFORMATION: Synthetic peptide

<400> SEQUENCE: 8

Ser Trp Leu Ser Lys Thr Ala Lys Lys Leu Glu Asn Ser Ala Lys Lys
1               5                   10                  15

Arg Ile Ser Glu Gly Ile Ala Ile Ala Ile Gln Gly Gly Pro Arg
            20                  25                  30

<210> SEQ ID NO 9
<211> LENGTH: 20
<212> TYPE: PRT
<213> ORGANISM: Artificial
<220> FEATURE:
<223> OTHER INFORMATION: Synthetic peptide

<400> SEQUENCE: 9

Ala Leu Phe Ser Leu Ala Ser Lys Val Val Pro Ser Val Phe Ser Met
1               5                   10                  15

Val Thr Lys Lys
            20

<210> SEQ ID NO 10
<211> LENGTH: 20
<212> TYPE: PRT
<213> ORGANISM: Artificial
<220> FEATURE:
<223> OTHER INFORMATION: Synthetic peptide

<400> SEQUENCE: 10

Val Val Phe Arg Val Ala Ser Lys Val Phe Pro Ala Val Tyr Cys Thr
1               5                   10                  15

Val Ser Lys Lys
            20

<210> SEQ ID NO 11
<211> LENGTH: 20
<212> TYPE: PRT
<213> ORGANISM: Artificial
<220> FEATURE:
<223> OTHER INFORMATION: Synthetic peptide

<400> SEQUENCE: 11

Ser Val Lys Val Ala Lys Ser Val Ile Pro Ser Ala Val Phe Ala Gly
1               5                   10                  15

Gly Lys Val Phe
```

-continued

```
                 20

<210> SEQ ID NO 12
<211> LENGTH: 20
<212> TYPE: PRT
<213> ORGANISM: Artificial
<220> FEATURE:
<223> OTHER INFORMATION: Synthetic peptide

<400> SEQUENCE: 12

Lys Val Val Leu Phe Gly Ala Ala Gly Ala Lys Leu Phe Lys Ala Ser
1               5                   10                  15

Phe Phe Gly Pro
            20

<210> SEQ ID NO 13
<211> LENGTH: 20
<212> TYPE: PRT
<213> ORGANISM: Artificial
<220> FEATURE:
<223> OTHER INFORMATION: Synthetic peptide

<400> SEQUENCE: 13

Phe Leu Phe Gly Leu Ala Ser Lys Val Phe Pro Ala Val Tyr Cys Lys
1               5                   10                  15

Val Thr Arg Lys
            20

<210> SEQ ID NO 14
<211> LENGTH: 20
<212> TYPE: PRT
<213> ORGANISM: Artificial
<220> FEATURE:
<223> OTHER INFORMATION: Synthetic peptide

<400> SEQUENCE: 14

Leu Ser Ala Val Gly Lys Ile Ala Ser Lys Val Val Pro Ser Val Ile
1               5                   10                  15

Gly Ala Phe Lys
            20

<210> SEQ ID NO 15
<211> LENGTH: 20
<212> TYPE: PRT
<213> ORGANISM: Artificial
<220> FEATURE:
<223> OTHER INFORMATION: Synthetic peptide

<400> SEQUENCE: 15

Pro Val Ile Gly Lys Leu Ala Ser Lys Val Pro Ser Val Phe Ser
1               5                   10                  15

Met Ile Lys Arg
            20

<210> SEQ ID NO 16
<211> LENGTH: 20
<212> TYPE: PRT
<213> ORGANISM: Artificial
<220> FEATURE:
<223> OTHER INFORMATION: Synthetic peptide

<400> SEQUENCE: 16

Lys Thr Val Pro Val Val Leu Lys Ala Ser Ile Lys Val Ser Ser Ala
1               5                   10                  15
```

```
Gly Phe Gly Phe
            20

<210> SEQ ID NO 17
<211> LENGTH: 20
<212> TYPE: PRT
<213> ORGANISM: Artificial
<220> FEATURE:
<223> OTHER INFORMATION: Synthetic peptide

<400> SEQUENCE: 17

Gly Leu Met Ser Leu Val Lys Asp Ile Ala Lys Leu Ala Ala Lys Gln
1               5                   10                  15

Gly Ala Lys Gln
            20

<210> SEQ ID NO 18
<211> LENGTH: 20
<212> TYPE: PRT
<213> ORGANISM: Artificial
<220> FEATURE:
<223> OTHER INFORMATION: Synthetic peptide

<400> SEQUENCE: 18

Thr His Ile His Met Asn Ala Arg Leu Leu Ile Arg Ser Pro Phe Thr
1               5                   10                  15

Asp Pro Gln Leu
            20

<210> SEQ ID NO 19
<211> LENGTH: 20
<212> TYPE: PRT
<213> ORGANISM: Artificial
<220> FEATURE:
<223> OTHER INFORMATION: Synthetic peptide

<400> SEQUENCE: 19

Val Ile Ala Phe Ala Lys Thr Lys Glu Ala Lys Ala Lys Leu Lys Gly
1               5                   10                  15

Gln Ala Lys Gly
            20

<210> SEQ ID NO 20
<211> LENGTH: 20
<212> TYPE: PRT
<213> ORGANISM: Artificial
<220> FEATURE:
<223> OTHER INFORMATION: Synthetic peptide

<400> SEQUENCE: 20

Gly Val Ser Ser Pro Ile Val Ala Val Lys Phe Lys Gly Ala Val Ala
1               5                   10                  15

Ser Leu Ile Lys
            20

<210> SEQ ID NO 21
<211> LENGTH: 20
<212> TYPE: PRT
<213> ORGANISM: Artificial
<220> FEATURE:
<223> OTHER INFORMATION: Synthetic peptide

<400> SEQUENCE: 21

Lys Ser Pro Phe Val Leu Val Val Ser Ser Arg Val Ala Ala Val Ile
1               5                   10                  15
```

```
Lys Ser Leu Pro
            20

<210> SEQ ID NO 22
<211> LENGTH: 20
<212> TYPE: PRT
<213> ORGANISM: Artificial
<220> FEATURE:
<223> OTHER INFORMATION: Synthetic peptide

<400> SEQUENCE: 22

Gly Leu Lys Lys Asp Ala Leu Gln Ser Ile Val Lys Lys Ala Gln Leu
1               5                   10                  15

Ala Ala Met Gly
            20

<210> SEQ ID NO 23
<211> LENGTH: 20
<212> TYPE: PRT
<213> ORGANISM: Artificial
<220> FEATURE:
<223> OTHER INFORMATION: Synthetic peptide

<400> SEQUENCE: 23

Ser Ala Leu Gly Arg Val Ala Ser Lys Val Phe Pro Ala Val Tyr Cys
1               5                   10                  15

Ser Ile Thr Lys
            20

<210> SEQ ID NO 24
<211> LENGTH: 20
<212> TYPE: PRT
<213> ORGANISM: Artificial
<220> FEATURE:
<223> OTHER INFORMATION: Synthetic peptide

<400> SEQUENCE: 24

Phe Leu Gly Gly Leu Ile Lys Ile Val Pro Ala Met Ile Cys Ala Val
1               5                   10                  15

Thr Lys Lys Cys
            20

<210> SEQ ID NO 25
<211> LENGTH: 20
<212> TYPE: PRT
<213> ORGANISM: Artificial
<220> FEATURE:
<223> OTHER INFORMATION: Synthetic peptide

<400> SEQUENCE: 25

Ser Val Pro Ser Val Gly Ala Val Leu Phe Phe Lys Arg Ala Ala Val
1               5                   10                  15

Met Lys Leu Ile
            20

<210> SEQ ID NO 26
<211> LENGTH: 20
<212> TYPE: PRT
<213> ORGANISM: Artificial
<220> FEATURE:
<223> OTHER INFORMATION: Synthetic peptide

<400> SEQUENCE: 26

Ser Ser Ser Ile Pro Ile Lys Met Val Leu Val Arg Ala Leu Val Phe
```

```
1               5                   10                  15
Val Lys Ser Gly
            20

<210> SEQ ID NO 27
<211> LENGTH: 20
<212> TYPE: PRT
<213> ORGANISM: Artificial
<220> FEATURE:
<223> OTHER INFORMATION: Synthetic peptide

<400> SEQUENCE: 27

Arg Lys Arg Lys Ser Asp Val Asp Phe Glu Ala Glu Phe Glu Leu Phe
1               5                   10                  15
Glu Asp Asp Asp
            20

<210> SEQ ID NO 28
<211> LENGTH: 26
<212> TYPE: PRT
<213> ORGANISM: Artificial
<220> FEATURE:
<223> OTHER INFORMATION: Synthetic peptide

<400> SEQUENCE: 28

Gly Ile Gly Ala Val Leu Lys Val Leu Thr Thr Gly Leu Pro Ala Leu
1               5                   10                  15
Ile Ser Trp Ile Lys Arg Lys Arg Gln Gln
            20                  25

<210> SEQ ID NO 29
<211> LENGTH: 20
<212> TYPE: PRT
<213> ORGANISM: Artificial
<220> FEATURE:
<223> OTHER INFORMATION: Synthetic peptide

<400> SEQUENCE: 29

Phe Met Lys Val Leu Ala Val Phe Gly Ser Val Val Thr Ser Ala Pro
1               5                   10                  15
Lys Ala Ser Lys
            20

<210> SEQ ID NO 30
<211> LENGTH: 20
<212> TYPE: PRT
<213> ORGANISM: Artificial
<220> FEATURE:
<223> OTHER INFORMATION: Synthetic peptide

<400> SEQUENCE: 30

Leu Gly Ala Leu Phe Arg Val Ala Ser Lys Val Phe Pro Ala Val Ile
1               5                   10                  15
Ser Met Val Lys
            20

<210> SEQ ID NO 31
<211> LENGTH: 20
<212> TYPE: PRT
<213> ORGANISM: Artificial
<220> FEATURE:
<223> OTHER INFORMATION: Synthetic peptide

<400> SEQUENCE: 31
```

-continued

```
Ala Leu Gly Lys Leu Ala Ser Lys Val Phe Pro Ala Val Tyr Cys Thr
1               5                   10                  15

Ile Ser Arg Lys
            20

<210> SEQ ID NO 32
<211> LENGTH: 20
<212> TYPE: PRT
<213> ORGANISM: Artificial
<220> FEATURE:
<223> OTHER INFORMATION: Synthetic peptide

<400> SEQUENCE: 32

Gly Phe Ile Gly Lys Leu Ala Ser Lys Val Val Pro Ser Val Tyr Cys
1               5                   10                  15

Lys Val Thr Gly
            20

<210> SEQ ID NO 33
<211> LENGTH: 20
<212> TYPE: PRT
<213> ORGANISM: Artificial
<220> FEATURE:
<223> OTHER INFORMATION: Synthetic peptide

<400> SEQUENCE: 33

Pro Val Val Phe Ser Val Ala Ser Lys Val Val Pro Ser Leu Ile Ser
1               5                   10                  15

Ala Leu Lys Arg
            20

<210> SEQ ID NO 34
<211> LENGTH: 20
<212> TYPE: PRT
<213> ORGANISM: Artificial
<220> FEATURE:
<223> OTHER INFORMATION: Synthetic peptide

<400> SEQUENCE: 34

Leu Pro Val Leu Phe Ser Ser Ala Ile Ala Lys Val Gly Ile Lys Leu
1               5                   10                  15

Gly Ala Lys Val
            20

<210> SEQ ID NO 35
<211> LENGTH: 20
<212> TYPE: PRT
<213> ORGANISM: Artificial
<220> FEATURE:
<223> OTHER INFORMATION: Synthetic peptide

<400> SEQUENCE: 35

Val Phe Ser Val Lys Gly Gly Lys Pro Ser Val Val Ile Lys Val Val
1               5                   10                  15

Val Ala Ser Thr
            20

<210> SEQ ID NO 36
<211> LENGTH: 20
<212> TYPE: PRT
<213> ORGANISM: Artificial
<220> FEATURE:
<223> OTHER INFORMATION: SYnthetic peptide

<400> SEQUENCE: 36
```

```
Phe Leu Gly Val Val Phe Lys Leu Ala Ser Lys Val Phe Pro Ala Val
1               5                   10                  15

Phe Gly Lys Val
            20

<210> SEQ ID NO 37
<211> LENGTH: 20
<212> TYPE: PRT
<213> ORGANISM: Artificial
<220> FEATURE:
<223> OTHER INFORMATION: Synthetic peptide

<400> SEQUENCE: 37

Pro Ala Val Phe Lys Ile Ala Ser Lys Val Val Pro Ser Val Tyr Cys
1               5                   10                  15

Lys Val Ser Arg
            20

<210> SEQ ID NO 38
<211> LENGTH: 20
<212> TYPE: PRT
<213> ORGANISM: Artificial
<220> FEATURE:
<223> OTHER INFORMATION: Synthetic peptide

<400> SEQUENCE: 38

Gly Ala Leu Phe Gly Leu Ala Ser Lys Val Phe Pro Ala Val Phe Gly
1               5                   10                  15

Ala Phe Lys Lys
            20

<210> SEQ ID NO 39
<211> LENGTH: 20
<212> TYPE: PRT
<213> ORGANISM: Artificial
<220> FEATURE:
<223> OTHER INFORMATION: Synthetic peptide

<400> SEQUENCE: 39

Ser Ala Val Gly Lys Leu Ala Ser Lys Val Phe Pro Ala Val Phe Ser
1               5                   10                  15

Met Val Thr Lys
            20

<210> SEQ ID NO 40
<211> LENGTH: 20
<212> TYPE: PRT
<213> ORGANISM: Artificial
<220> FEATURE:
<223> OTHER INFORMATION: Synthetic peptide

<400> SEQUENCE: 40

Thr Ala Lys Val Val Val Phe Val Ser Phe Ser Tyr Val Val Pro Lys
1               5                   10                  15

Lys Arg Ala Cys
            20

<210> SEQ ID NO 41
<211> LENGTH: 20
<212> TYPE: PRT
<213> ORGANISM: Artificial
<220> FEATURE:
<223> OTHER INFORMATION: Synthetic peptide
```

```
<400> SEQUENCE: 41

Val Lys Asp Leu Ala Lys Phe Ile Ala Lys Thr Val Ala Lys Gln Gly
1               5                   10                  15

Gly Cys Tyr Leu
            20

<210> SEQ ID NO 42
<211> LENGTH: 20
<212> TYPE: PRT
<213> ORGANISM: Artificial
<220> FEATURE:
<223> OTHER INFORMATION: Synthetic peptide

<400> SEQUENCE: 42

Gly Val Val Gly Lys Leu Ala Ser Lys Val Pro Ser Val Phe Gly
1               5                   10                  15

Ser Phe Thr Lys
            20

<210> SEQ ID NO 43
<211> LENGTH: 20
<212> TYPE: PRT
<213> ORGANISM: Artificial
<220> FEATURE:
<223> OTHER INFORMATION: Synthetic peptide

<400> SEQUENCE: 43

Leu Pro Val Val Phe Arg Val Ala Ser Lys Val Phe Pro Ala Leu Ile
1               5                   10                  15

Ser Lys Leu Thr
            20

<210> SEQ ID NO 44
<211> LENGTH: 20
<212> TYPE: PRT
<213> ORGANISM: Artificial
<220> FEATURE:
<223> OTHER INFORMATION: Synthetic peptide

<400> SEQUENCE: 44

Ser Ala Val Gly Ser Val Ala Ser Lys Val Val Pro Ser Leu Ile Ser
1               5                   10                  15

Lys Val Thr Lys
            20

<210> SEQ ID NO 45
<211> LENGTH: 20
<212> TYPE: PRT
<213> ORGANISM: Artificial
<220> FEATURE:
<223> OTHER INFORMATION: SYnthetic peptide

<400> SEQUENCE: 45

Ser Lys Phe Pro Leu Ala Gly Ile Phe Ser Val Pro Gly Val Lys Arg
1               5                   10                  15

Val Val Val Ile
            20

<210> SEQ ID NO 46
<211> LENGTH: 20
<212> TYPE: PRT
<213> ORGANISM: Artificial
<220> FEATURE:
<223> OTHER INFORMATION: Synthetic peptide
```

```
<400> SEQUENCE: 46

Ala Ala Thr Gly Thr Gly Lys Thr Ala Ala Phe Ala Leu Pro Val Leu
1               5                   10                  15

Glu Arg Leu Ile
            20

<210> SEQ ID NO 47
<211> LENGTH: 20
<212> TYPE: PRT
<213> ORGANISM: Artificial
<220> FEATURE:
<223> OTHER INFORMATION: Synthetic peptide

<400> SEQUENCE: 47

Met Lys Ser Ile Ala Lys Phe Ile Ala Lys Thr Val Ala Lys Gln Gly
1               5                   10                  15

Ala Lys Gln Gly
            20

<210> SEQ ID NO 48
<211> LENGTH: 23
<212> TYPE: PRT
<213> ORGANISM: Artificial
<220> FEATURE:
<223> OTHER INFORMATION: Synthetic peptide

<400> SEQUENCE: 48

Gly Ile Gly Lys Phe Leu His Ser Ala Lys Lys Phe Gly Lys Ala Phe
1               5                   10                  15

Val Gly Glu Ile Met Asn Ser
            20

<210> SEQ ID NO 49
<211> LENGTH: 20
<212> TYPE: PRT
<213> ORGANISM: Artificial
<220> FEATURE:
<223> OTHER INFORMATION: Synthetic peptide

<400> SEQUENCE: 49

Ile Cys Ile Phe Cys Cys Gly Cys Cys His Arg Ser Lys Cys Gly Met
1               5                   10                  15

Cys Cys Lys Thr
            20

<210> SEQ ID NO 50
<211> LENGTH: 20
<212> TYPE: PRT
<213> ORGANISM: Artificial
<220> FEATURE:
<223> OTHER INFORMATION: Synthetic peptide

<400> SEQUENCE: 50

Leu Pro Ala Val Phe Lys Leu Ala Ser Lys Val Val Pro Ser Val Phe
1               5                   10                  15

Gly Leu Val Lys
            20

<210> SEQ ID NO 51
<211> LENGTH: 20
<212> TYPE: PRT
<213> ORGANISM: Artificial
<220> FEATURE:
```

<223> OTHER INFORMATION: Synthetic peptide

<400> SEQUENCE: 51

Ser Phe Val Phe Lys Leu Ala Ser Lys Val Val Pro Ser Val Phe Ser
1               5                   10                  15

Ala Leu Thr Arg
        20

<210> SEQ ID NO 52
<211> LENGTH: 20
<212> TYPE: PRT
<213> ORGANISM: Artificial
<220> FEATURE:
<223> OTHER INFORMATION: Synthetic peptide

<400> SEQUENCE: 52

Ser Val Ile Gly Lys Ile Ala Ser Lys Val Val Pro Ser Val Tyr Cys
1               5                   10                  15

Ala Ile Ser Lys
        20

<210> SEQ ID NO 53
<211> LENGTH: 20
<212> TYPE: PRT
<213> ORGANISM: Artificial
<220> FEATURE:
<223> OTHER INFORMATION: Synthetic peptide

<400> SEQUENCE: 53

Pro Val Val Gly Arg Val Ala Ser Lys Val Phe Pro Ala Val Ile Gly
1               5                   10                  15

Leu Val Lys Lys
        20

<210> SEQ ID NO 54
<211> LENGTH: 20
<212> TYPE: PRT
<213> ORGANISM: Artificial
<220> FEATURE:
<223> OTHER INFORMATION: Synthetic peptide

<400> SEQUENCE: 54

Val Ser Val Lys Lys Val Leu Pro Phe Ala Pro Leu Lys Ser Leu Leu
1               5                   10                  15

Ser Phe Ala Phe
        20

<210> SEQ ID NO 55
<211> LENGTH: 20
<212> TYPE: PRT
<213> ORGANISM: Artificial
<220> FEATURE:
<223> OTHER INFORMATION: Synthetic peptide

<400> SEQUENCE: 55

Asn Val Pro Gly Val Glu Tyr Tyr Glu Ile Glu Thr Gly Leu Gly Lys
1               5                   10                  15

Phe Lys Tyr Ala
        20

<210> SEQ ID NO 56
<211> LENGTH: 20
<212> TYPE: PRT
<213> ORGANISM: Artificial

```
<220> FEATURE:
<223> OTHER INFORMATION: Synthetic peptide

<400> SEQUENCE: 56

Gly Val Ser Val Ala Gly Ala Lys Lys Val Lys Val Leu Phe Val Phe
1               5                   10                  15

Pro Phe Leu Phe
            20

<210> SEQ ID NO 57
<211> LENGTH: 20
<212> TYPE: PRT
<213> ORGANISM: Artificial
<220> FEATURE:
<223> OTHER INFORMATION: Synthetic peptide

<400> SEQUENCE: 57

Arg Lys Val Ala Pro Ala Leu Ile Lys Ser Phe Val Phe Leu Phe Lys
1               5                   10                  15

Phe Lys Lys Gly
            20

<210> SEQ ID NO 58
<211> LENGTH: 20
<212> TYPE: PRT
<213> ORGANISM: Artificial
<220> FEATURE:
<223> OTHER INFORMATION: Synthetic peptide

<400> SEQUENCE: 58

Pro Tyr Ser Leu Lys Asn Gly Glu Asn Trp Leu Leu Ser Glu Glu Ile
1               5                   10                  15

Ile Arg Tyr Pro
            20

<210> SEQ ID NO 59
<211> LENGTH: 20
<212> TYPE: PRT
<213> ORGANISM: Artificial
<220> FEATURE:
<223> OTHER INFORMATION: Synthetic peptide

<400> SEQUENCE: 59

Phe Leu Phe Arg Val Ala Ser Lys Val Phe Pro Ala Leu Ile Gly Lys
1               5                   10                  15

Phe Lys Lys Lys
            20

<210> SEQ ID NO 60
<211> LENGTH: 20
<212> TYPE: PRT
<213> ORGANISM: Artificial
<220> FEATURE:
<223> OTHER INFORMATION: Synthetic peptide

<400> SEQUENCE: 60

Leu Tyr Ser Pro Thr Cys Val Lys Ala Ala Val Ser Arg Phe Ile Gly
1               5                   10                  15

Lys Val Ser Ala
            20

<210> SEQ ID NO 61
<211> LENGTH: 20
<212> TYPE: PRT
```

```
<213> ORGANISM: Artificial
<220> FEATURE:
<223> OTHER INFORMATION: Synthetic peptide

<400> SEQUENCE: 61

Ser Thr Val Lys Val Ala Ser Lys Leu Ala Val Val Ser Pro Ile
1               5                   10                  15

Ser Lys Gly Ser
            20

<210> SEQ ID NO 62
<211> LENGTH: 20
<212> TYPE: PRT
<213> ORGANISM: Artificial
<220> FEATURE:
<223> OTHER INFORMATION: Synthetic peptide

<400> SEQUENCE: 62

Phe Lys Val Val Ile Ser Lys Pro Gly Leu Ser Val Arg Val Gly Thr
1               5                   10                  15

Ala Leu Val Thr
            20

<210> SEQ ID NO 63
<211> LENGTH: 20
<212> TYPE: PRT
<213> ORGANISM: Artificial
<220> FEATURE:
<223> OTHER INFORMATION: Synthetic peptide

<400> SEQUENCE: 63

Leu Ser Phe Val Gly Arg Val Ala Ser Lys Val Val Pro Ser Leu Ile
1               5                   10                  15

Ser Met Ile Lys
            20

<210> SEQ ID NO 64
<211> LENGTH: 20
<212> TYPE: PRT
<213> ORGANISM: Artificial
<220> FEATURE:
<223> OTHER INFORMATION: Synthetic peptide

<400> SEQUENCE: 64

Ser Ala Leu Gly Arg Leu Ala Ser Lys Val Val Pro Ala Val Ile Gly
1               5                   10                  15

Lys Val Thr Thr
            20

<210> SEQ ID NO 65
<211> LENGTH: 20
<212> TYPE: PRT
<213> ORGANISM: Artificial
<220> FEATURE:
<223> OTHER INFORMATION: Synthetic peptide

<400> SEQUENCE: 65

Leu Gly Val Val Gly Ser Leu Ala Ser Lys Val Val Pro Ala Val Ile
1               5                   10                  15

Ser Lys Val Lys
            20

<210> SEQ ID NO 66
<211> LENGTH: 20
```

```
<212> TYPE: PRT
<213> ORGANISM: Artificial
<220> FEATURE:
<223> OTHER INFORMATION: Synthetic peptide

<400> SEQUENCE: 66

Val Lys Arg Ala Gly Lys Gly Val Ala Val Val Pro Ser Pro Leu Phe
1               5                   10                  15

Lys Ile Val Val
            20

<210> SEQ ID NO 67
<211> LENGTH: 20
<212> TYPE: PRT
<213> ORGANISM: Artificial
<220> FEATURE:
<223> OTHER INFORMATION: Synthetic peptide

<400> SEQUENCE: 67

Ile Ala Ser Ala Val Pro Val Cys Val Lys Gly Lys Ile Ser Lys Ser
1               5                   10                  15

Tyr Ile Ser Val
            20

<210> SEQ ID NO 68
<211> LENGTH: 20
<212> TYPE: PRT
<213> ORGANISM: Artificial
<220> FEATURE:
<223> OTHER INFORMATION: Synthetic peptide

<400> SEQUENCE: 68

Lys Trp Lys Leu Phe Lys Lys Ile Gly Ile Gly Lys Phe Leu His Ser
1               5                   10                  15

Ala Lys Lys Phe
            20

<210> SEQ ID NO 69
<211> LENGTH: 20
<212> TYPE: PRT
<213> ORGANISM: Artificial
<220> FEATURE:
<223> OTHER INFORMATION: Synthetic peptide

<400> SEQUENCE: 69

Ala Leu Val Tyr Ala Gly Ile Lys Lys Thr Ala Phe Leu Lys Val Gln
1               5                   10                  15

Lys Cys Asp Gly
            20

<210> SEQ ID NO 70
<211> LENGTH: 20
<212> TYPE: PRT
<213> ORGANISM: Artificial
<220> FEATURE:
<223> OTHER INFORMATION: Synthetic peptide

<400> SEQUENCE: 70

Leu Pro Ala Val Phe Lys Leu Ala Ser Lys Val Phe Pro Ala Val Tyr
1               5                   10                  15

Cys Lys Ala Ser
            20

<210> SEQ ID NO 71
```

```
<211> LENGTH: 20
<212> TYPE: PRT
<213> ORGANISM: Artificial
<220> FEATURE:
<223> OTHER INFORMATION: Synthetic peptide

<400> SEQUENCE: 71

Leu Pro Val Leu Phe Lys Leu Ala Ser Lys Val Phe Pro Ala Val Phe
1               5                   10                  15

Ser Ser Leu Lys
            20

<210> SEQ ID NO 72
<211> LENGTH: 20
<212> TYPE: PRT
<213> ORGANISM: Artificial
<220> FEATURE:
<223> OTHER INFORMATION: Synthetic peptide

<400> SEQUENCE: 72

Ser Ile His Ile Gly Pro Gly Arg Ala Phe Tyr Ala Thr Gly Asn Ile
1               5                   10                  15

Ile Gly Asp Ile
            20

<210> SEQ ID NO 73
<211> LENGTH: 20
<212> TYPE: PRT
<213> ORGANISM: Artificial
<220> FEATURE:
<223> OTHER INFORMATION: Synthetic peptide

<400> SEQUENCE: 73

Val Val Gly Arg Val Ala Ser Lys Val Val Pro Ser Leu Ile Gly Leu
1               5                   10                  15

Phe Thr Thr Lys
            20

<210> SEQ ID NO 74
<211> LENGTH: 20
<212> TYPE: PRT
<213> ORGANISM: Artificial
<220> FEATURE:
<223> OTHER INFORMATION: Synthetic peptide

<400> SEQUENCE: 74

Gly Gly Ser Thr Leu Gly Val Phe Val Lys Lys Ser Lys Ala Cys Val
1               5                   10                  15

Ile Val Pro Tyr
            20

<210> SEQ ID NO 75
<211> LENGTH: 19
<212> TYPE: PRT
<213> ORGANISM: Artificial
<220> FEATURE:
<223> OTHER INFORMATION: Synthetic peptide

<400> SEQUENCE: 75

Lys Gly Arg Gly Lys Gln Gly Gly Lys Val Arg Ala Lys Ala Lys Thr
1               5                   10                  15

Arg Ser Ser

<210> SEQ ID NO 76
```

-continued

```
<211> LENGTH: 20
<212> TYPE: PRT
<213> ORGANISM: Artificial
<220> FEATURE:
<223> OTHER INFORMATION: Synthetic peptide

<400> SEQUENCE: 76

Ser Arg Val Pro Leu Lys Ser Pro Val Lys Ile Val Gly Ser Lys Val
1               5                   10                  15

Met Ile Phe Ala
            20

<210> SEQ ID NO 77
<211> LENGTH: 20
<212> TYPE: PRT
<213> ORGANISM: Artificial
<220> FEATURE:
<223> OTHER INFORMATION: Synthetic peptide

<400> SEQUENCE: 77

Ser Val Val Phe Gly Val Ala Ser Lys Val Val Pro Ser Val Ile Gly
1               5                   10                  15

Lys Val Lys Thr
            20

<210> SEQ ID NO 78
<211> LENGTH: 20
<212> TYPE: PRT
<213> ORGANISM: Artificial
<220> FEATURE:
<223> OTHER INFORMATION: Synthetic peptide

<400> SEQUENCE: 78

Pro Lys Val Val Gly Leu Ser Ile Val Val Lys Ala Lys Val Ser
1               5                   10                  15

Ser Ala Leu Gly
            20

<210> SEQ ID NO 79
<211> LENGTH: 20
<212> TYPE: PRT
<213> ORGANISM: Artificial
<220> FEATURE:
<223> OTHER INFORMATION: Synthetic peptide

<400> SEQUENCE: 79

Phe Leu Pro Val Leu Val Lys Val Phe Arg Tyr Ser Lys Lys Thr Ala
1               5                   10                  15

Ala Gly Cys Phe
            20

<210> SEQ ID NO 80
<211> LENGTH: 14
<212> TYPE: PRT
<213> ORGANISM: Artificial
<220> FEATURE:
<223> OTHER INFORMATION: Synthetic peptide

<400> SEQUENCE: 80

Lys Trp Lys Leu Phe Lys Lys Ile Gly Ala Val Leu Lys Val
1               5                   10

<210> SEQ ID NO 81
<211> LENGTH: 20
<212> TYPE: PRT
```

```
<213> ORGANISM: Artificial
<220> FEATURE:
<223> OTHER INFORMATION: Synthetic peptide

<400> SEQUENCE: 81

Met Val Val Phe Ser Val Pro Lys Phe Lys Ser Thr Val Ala Lys Leu
1               5                   10                  15

Leu Ser Ser Ala
            20

<210> SEQ ID NO 82
<211> LENGTH: 20
<212> TYPE: PRT
<213> ORGANISM: Artificial
<220> FEATURE:
<223> OTHER INFORMATION: Synthetic peptide

<400> SEQUENCE: 82

Lys Phe Asp Pro Leu Glu Gly Ala Pro Met Ala Arg Gly Ile Val Leu
1               5                   10                  15

Glu Lys Val Gly
            20

<210> SEQ ID NO 83
<211> LENGTH: 20
<212> TYPE: PRT
<213> ORGANISM: Artificial
<220> FEATURE:
<223> OTHER INFORMATION: Synthetic peptide

<400> SEQUENCE: 83

Phe Leu Pro Phe Val Gly Arg Ile Ala Ser Lys Val Val Pro Ser Val
1               5                   10                  15

Ile Gly Lys Val
            20

<210> SEQ ID NO 84
<211> LENGTH: 20
<212> TYPE: PRT
<213> ORGANISM: Artificial
<220> FEATURE:
<223> OTHER INFORMATION: SYnthetic peptide

<400> SEQUENCE: 84

Thr Leu Val Gly Val Val Ala Lys Leu Val Ala Thr Lys Ile Gly Ser
1               5                   10                  15

Ser Pro Arg Ala
            20

<210> SEQ ID NO 85
<211> LENGTH: 20
<212> TYPE: PRT
<213> ORGANISM: Artificial
<220> FEATURE:
<223> OTHER INFORMATION: Synthetic peptide

<400> SEQUENCE: 85

Gly Lys Lys Leu Ala Lys Thr Ile Ala Lys Glu Val Ala Lys Gln Gly
1               5                   10                  15

Ala Lys Phe Ala
            20

<210> SEQ ID NO 86
<211> LENGTH: 20
```

```
<212> TYPE: PRT
<213> ORGANISM: Artificial
<220> FEATURE:
<223> OTHER INFORMATION: Synthetic peptide

<400> SEQUENCE: 86

Ser Val Lys Pro Val Gly Ser Ser Val Val Lys Gly Thr Ala Leu Val
1               5                   10                  15

Lys Phe Phe Gly
            20

<210> SEQ ID NO 87
<211> LENGTH: 20
<212> TYPE: PRT
<213> ORGANISM: Artificial
<220> FEATURE:
<223> OTHER INFORMATION: Synthetic peptide

<400> SEQUENCE: 87

Ala Ser Pro Thr Val Phe Arg Ser Ser Val Phe Leu Ser Leu Phe Val
1               5                   10                  15

Val Ala Lys Lys
            20

<210> SEQ ID NO 88
<211> LENGTH: 20
<212> TYPE: PRT
<213> ORGANISM: Artificial
<220> FEATURE:
<223> OTHER INFORMATION: SYnthetic peptide

<400> SEQUENCE: 88

Lys Val Phe Ile Ala Thr Leu Val Val Ser Ser Phe Leu Leu Ala Lys
1               5                   10                  15

Pro Pro Arg Val
            20

<210> SEQ ID NO 89
<211> LENGTH: 20
<212> TYPE: PRT
<213> ORGANISM: Artificial
<220> FEATURE:
<223> OTHER INFORMATION: Synthetic peptide

<400> SEQUENCE: 89

Pro Phe Val Gly Arg Val Ala Ser Lys Val Val Pro Ser Val Tyr Cys
1               5                   10                  15

Ala Ile Thr Arg
            20

<210> SEQ ID NO 90
<211> LENGTH: 20
<212> TYPE: PRT
<213> ORGANISM: Artificial
<220> FEATURE:
<223> OTHER INFORMATION: Synthetic peptide

<400> SEQUENCE: 90

Phe Val Gly Ser Leu Ala Ser Lys Val Val Pro Ser Val Phe Gly Ala
1               5                   10                  15

Ile Lys Thr Lys
            20

<210> SEQ ID NO 91
```

```
<211> LENGTH: 20
<212> TYPE: PRT
<213> ORGANISM: Artificial
<220> FEATURE:
<223> OTHER INFORMATION: Synthetic peptide

<400> SEQUENCE: 91

Leu Pro Val Val Phe Lys Ile Ala Ser Lys Val Val Pro Ser Val Ile
1               5                   10                  15

Ser Lys Ile Thr
            20

<210> SEQ ID NO 92
<211> LENGTH: 20
<212> TYPE: PRT
<213> ORGANISM: Artificial
<220> FEATURE:
<223> OTHER INFORMATION: SYnthetic peptide

<400> SEQUENCE: 92

Gly Ala Val Phe Gly Val Ala Ser Lys Val Val Pro Ser Val Phe Ser
1               5                   10                  15

Ala Ile Lys Lys
            20

<210> SEQ ID NO 93
<211> LENGTH: 20
<212> TYPE: PRT
<213> ORGANISM: Artificial
<220> FEATURE:
<223> OTHER INFORMATION: Synthetic peptide

<400> SEQUENCE: 93

Phe Val Gly Gly Val Ala Ser Lys Val Val Pro Ser Val Tyr Cys Lys
1               5                   10                  15

Val Ser Lys Lys
            20

<210> SEQ ID NO 94
<211> LENGTH: 20
<212> TYPE: PRT
<213> ORGANISM: Artificial
<220> FEATURE:
<223> OTHER INFORMATION: Synthetic peptide

<400> SEQUENCE: 94

His Thr Gly Arg Ser Gly Pro Ala Thr Gly His Ser Gly His Ser Ser
1               5                   10                  15

Thr His Gly Ser
            20

<210> SEQ ID NO 95
<211> LENGTH: 20
<212> TYPE: PRT
<213> ORGANISM: Artificial
<220> FEATURE:
<223> OTHER INFORMATION: Synthetic peptide

<400> SEQUENCE: 95

Val Val Ala Lys Lys Phe Phe Val Leu Val Lys Gly Leu Ala Pro Val
1               5                   10                  15

Leu Ser Pro Ser
            20
```

```
<210> SEQ ID NO 96
<211> LENGTH: 20
<212> TYPE: PRT
<213> ORGANISM: Artificial
<220> FEATURE:
<223> OTHER INFORMATION: Synthetic peptide

<400> SEQUENCE: 96

Val Val Phe Lys Leu Ala Ser Lys Val Val Pro Ser Val Tyr Cys Thr
1               5                   10                  15

Ile Thr Lys Lys
            20

<210> SEQ ID NO 97
<211> LENGTH: 20
<212> TYPE: PRT
<213> ORGANISM: Artificial
<220> FEATURE:
<223> OTHER INFORMATION: Synthetic peptide

<400> SEQUENCE: 97

Lys Ile Val Lys Val Ile Thr Val Lys Ser Ile Ser Pro Ala Ser Leu
1               5                   10                  15

Val Pro Val Phe
            20

<210> SEQ ID NO 98
<211> LENGTH: 20
<212> TYPE: PRT
<213> ORGANISM: Artificial
<220> FEATURE:
<223> OTHER INFORMATION: Synthetic peptide

<400> SEQUENCE: 98

Pro Ser Leu Leu Tyr Lys Ala Lys Ala Val Phe Cys Lys Pro Ser Ala
1               5                   10                  15

Val Ala Val Phe
            20

<210> SEQ ID NO 99
<211> LENGTH: 20
<212> TYPE: PRT
<213> ORGANISM: Artificial
<220> FEATURE:
<223> OTHER INFORMATION: Synthetic peptide

<400> SEQUENCE: 99

Lys Val Gly Lys Gly Ser Tyr Pro Cys Ser Phe Val Lys Val Val Ala
1               5                   10                  15

Lys Val Ser Val
            20

<210> SEQ ID NO 100
<211> LENGTH: 20
<212> TYPE: PRT
<213> ORGANISM: Artificial
<220> FEATURE:
<223> OTHER INFORMATION: SYnthetic peptide

<400> SEQUENCE: 100

Val Lys Thr Lys Cys Ser Val Pro Ala Val Val Tyr Ile Leu Val Lys
1               5                   10                  15

Thr Phe Lys Ser
            20
```

```
<210> SEQ ID NO 101
<211> LENGTH: 20
<212> TYPE: PRT
<213> ORGANISM: Artificial
<220> FEATURE:
<223> OTHER INFORMATION: Synthetic peptide

<400> SEQUENCE: 101

Lys Tyr Gly Pro Ala Leu Val Ile Ala Val Lys Ser Cys Ser Leu
1               5                   10                  15

Thr Phe Arg Ala
            20

<210> SEQ ID NO 102
<211> LENGTH: 20
<212> TYPE: PRT
<213> ORGANISM: Artificial
<220> FEATURE:
<223> OTHER INFORMATION: Synthetic peptide

<400> SEQUENCE: 102

Ala Lys Lys Ala Gln Lys Ser Gly Ala Gln Thr Ile Val Lys Ile Phe
1               5                   10                  15

Ala Lys Gly Met
            20

<210> SEQ ID NO 103
<211> LENGTH: 20
<212> TYPE: PRT
<213> ORGANISM: Artificial
<220> FEATURE:
<223> OTHER INFORMATION: Synthetic peptide

<400> SEQUENCE: 103

Pro Ala Val Tyr Lys Ser Ile Val Gly Phe Ser Pro Val Ala Arg Val
1               5                   10                  15

Thr Val Cys Arg
            20

<210> SEQ ID NO 104
<211> LENGTH: 19
<212> TYPE: PRT
<213> ORGANISM: Artificial
<220> FEATURE:
<223> OTHER INFORMATION: Synthetic peptide

<400> SEQUENCE: 104

Ala Leu Phe Ser Leu Ala Ser Lys Val Val Pro Ala Val Ile Gly Leu
1               5                   10                  15

Ile Lys Lys

<210> SEQ ID NO 105
<211> LENGTH: 20
<212> TYPE: PRT
<213> ORGANISM: Artificial
<220> FEATURE:
<223> OTHER INFORMATION: Synthetic peptide

<400> SEQUENCE: 105

Ala Val Leu Phe Val Met Phe Leu Ser Leu Ile Gly Leu Leu Ala Ile
1               5                   10                  15

Ala Gly Ile Arg
            20
```

```
<210> SEQ ID NO 106
<211> LENGTH: 20
<212> TYPE: PRT
<213> ORGANISM: Artificial
<220> FEATURE:
<223> OTHER INFORMATION: Synthetic peptide

<400> SEQUENCE: 106

Lys Val Tyr Val Val Lys Ile Ala Val Pro Cys Phe Pro Lys Ser Ala
1               5                   10                  15

Arg Ser Val Ser
            20

<210> SEQ ID NO 107
<211> LENGTH: 20
<212> TYPE: PRT
<213> ORGANISM: Artificial
<220> FEATURE:
<223> OTHER INFORMATION: Synthetic peptide

<400> SEQUENCE: 107

Val Asp Lys Gly Ser Tyr Leu Pro Arg Pro Thr Pro Pro Arg Pro Ile
1               5                   10                  15

Tyr Asn Arg Asn
            20

<210> SEQ ID NO 108
<211> LENGTH: 21
<212> TYPE: PRT
<213> ORGANISM: Artificial
<220> FEATURE:
<223> OTHER INFORMATION: Querry sequence

<400> SEQUENCE: 108

Met Lys Ser Thr Gly Pro Leu Leu Ser Ala Leu Leu Leu Ala Val Thr
1               5                   10                  15

Ala Gly Gly Asp Pro
            20

<210> SEQ ID NO 109
<211> LENGTH: 7
<212> TYPE: PRT
<213> ORGANISM: Artificial
<220> FEATURE:
<223> OTHER INFORMATION: Grammer sequence

<400> SEQUENCE: 109

Lys Gln Arg Gln Thr His Ala
1               5

<210> SEQ ID NO 110
<211> LENGTH: 6
<212> TYPE: PRT
<213> ORGANISM: Artificial
<220> FEATURE:
<223> OTHER INFORMATION: Grammer sequence

<400> SEQUENCE: 110

Arg Leu Met Gly Ala Gly
1               5

<210> SEQ ID NO 111
<211> LENGTH: 10
<212> TYPE: PRT
<213> ORGANISM: Artificial
```

```
-continued

<220> FEATURE:
<223> OTHER INFORMATION: Grammer sequence

<400> SEQUENCE: 111

Arg Leu Leu Met Arg Gln Gln Thr His Ala
1               5                   10
```

METHODS AND SYSTEMS FOR GENERATING AND EVALUATING PEPTIDES

CROSS-REFERENCE TO RELATED APPLICATIONS

This application claims priority to and benefit of Provisional U.S. Patent Application No. 60/737,654 filed on Nov. 17, 2005.

FIELD OF THE INVENTION

Background of the Invention

Recently, advances have been made in synthesizing stable proteins with novel sequences. Efforts to design proteins rely largely on knowledge of the physical properties that determine protein structure, such as the patterns of hydrophobic and hydrophilic residues in the sequence, salt bridges and hydrogen bonds, and secondary structural preferences of amino acids. Various approaches to apply these principles have been attempted. For example, helical proteins were generated and discussed in Regan, et al., Science 241:976-978 (1988) and an experimental method was developed using random mutagenesis and described in Kamtekar, et al., Science 262:1680-1685 (1993). Similarly, U.S. Pat. No. 6,708,120 discusses a method that starts with a protein backbone structure and then modifies the backbone structure by establishing a group of potential rotamers for each of the variable residue positions in the backbone. The process then quantitatively analyzes and evaluates the interaction of each of the potential rotamers with all or part of the remainder of the protein backbone. Through this process, the method attempts to generate a set of optimized protein sequences. Additionally, de novo protein design has been discussed that proposes fully automated sequence selection. Dahiyat, B. I., and Mayo, S. L., De novo Protein Design: Fully Automated Sequence Selection. Science 278, 82 (1997). This work demonstrated a computational design algorithm based on physical-chemical potential functions and stereochemical constraints. The constraints were used to screen a combinatorial library of possible amino acid sequences for compatibility with a design target. Through this algorithm, non-wild type proteins were designed, as confirmed by BLAST searches, that had a compact well-ordered structure, in agreement with the design target.

Although these approaches have brought some clarity and discipline to the process of peptide design, the standard approach today is still to synthesize new peptides by creating synthesized peptides that look very similar to a known peptide having a particular function or purpose. The hope is that the synthesized peptide will have similar functionality to the naturally occurring peptide, and minimal or no side effects. The standard method is still employed today because synthesizing peptides is relatively simple and the currently developed approaches for computationally determining peptide sequences of interest are difficult to implement and offer only marginal improvement over heuristic sequence selection. Further, the existing processes have been limited in scope in as much as they typically begin from a starting point that is related to or defined by a single protein or peptide of interest. This tends to provide a narrow focus for the later development processes, and keeps newly developed proteins tightly bound to the selected seed sequence.

Thus, there is a need in the art for sequence design processes that provide a more comprehensive and methodical approach to protein design. There is also a need for a method that provides many product candidates rapidly and efficiently.

It is an object of the invention to provide design processes for proteins and other biological molecules that can be used to create a comprehensive database of peptides and grammars.

It is another object of the invention to provide peptide databases and design patterns or grammars for designing and constructing the databases.

SUMMARY OF THE INVENTION

A method has been developed to create databases of peptides having a desirable property, such as antimicrobial activity, based on analyzing a database of known peptides for a pattern statistically associated with an activity. One can determine a set of patterns that may be representative of a peptide having a desired characteristic or property, and evaluate a set of sequences against the set of patterns (grammars) to determine if the peptide sequence being evaluated has similar patterns to those of a peptide having the desired characteristic or property. The set of sequences being evaluated may include peptide sequences of a desired length comprising all or substantially all combinations of amino acids that conform to at least one of the set of patterns. Once the database is identified, the database is processed in a pattern recognition procedure that identifies a set of patterns representative of a peptide having the characteristic of interest. A set of newly generated peptides sequences may then be processed to score these new sequences against the identified patterns to correlate the patterns to the sequences and determine a degree of association or a similarity between a respective one of the new sequences and the set of identified patterns. The method is used to provide a database of sequences that are expected to have one or more desired activities, specific sequences within the database proven to have the desired activity, and the patterns or grammars used to create the database of sequences.

Although described with reference to antimicrobial peptides, a database of peptides may be identified that contains peptides that have antiviral properties, wound response properties, or some other property of interest. A new peptide sequence generated in such a manner may include one or more amino acids that match a chain of one or more amino acids at a pattern. Such a set comprising new peptide sequences of a desired length conforming to at least one of the set of patterns that are representative of peptides having the characteristic of interest are known as a conformal set. Optionally, the set of new peptide sequences may be generated by overlapping the grammars to exhaustively create all sequences that are covered by grammars starting at each amino acid position. The set of new sequences also may be chosen as a subset of sequences from the conformal set in other ways.

In another method, the process begins with a set of all or substantially all possible peptide sequences that conform to at least one of the set of patterns that are representative of peptides having the characteristic of interest and then tests these sequences against the set of identified patterns to identify a subset of the tested sequences that correlate sufficiently strongly to the patterns to indicate that the respective sequence likely exhibits the characteristic of interest. In a further optional practice, all sequences may be enumerated which are covered by grammars starting at each position.

In a further optional process, the systems and methods described herein may be employed to design peptides having two or more characteristics of interest. For example, the methods described herein may be employed to design peptides having a first characteristic, such as being antimicrobial, and a second characteristic such as having an acceptable level of toxicity.

DETAILED DESCRIPTION OF THE INVENTION

I. Definitions

Figure 1:
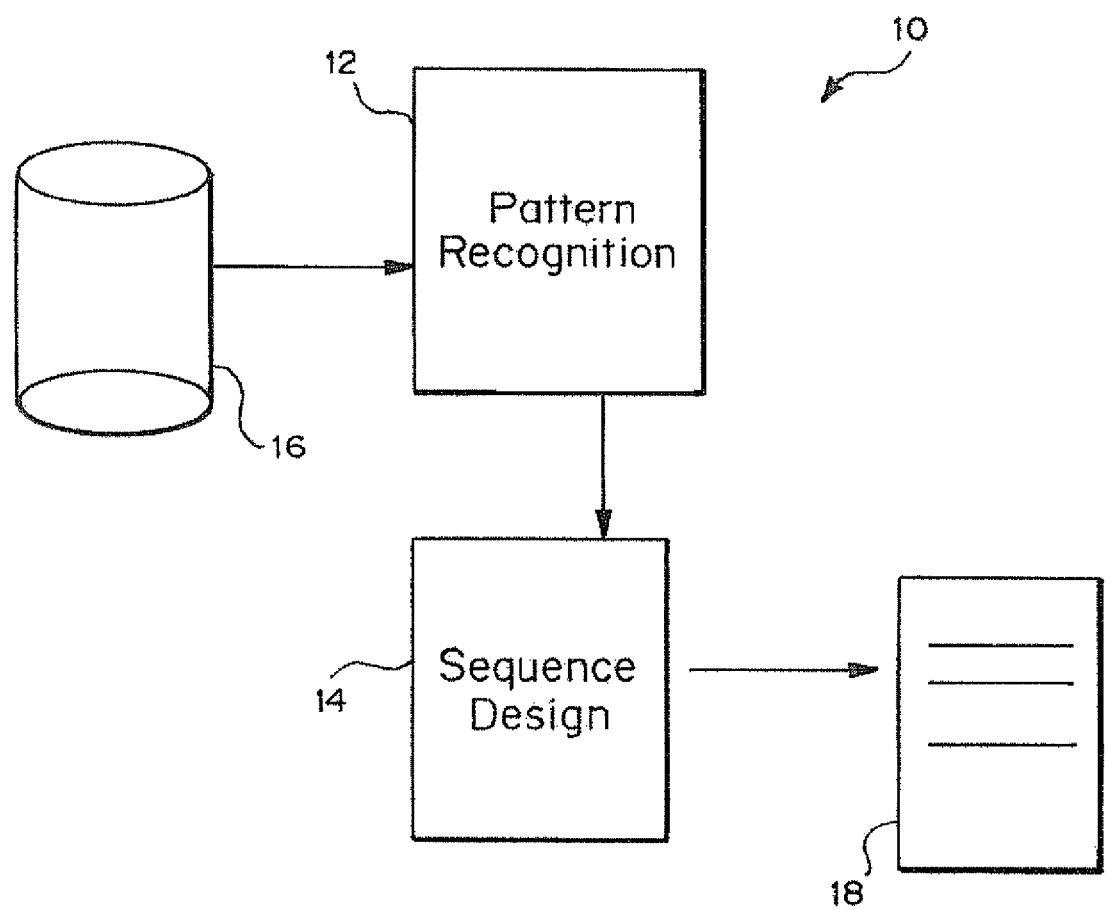
FIG. 1 depicts a functional block diagram representative of the process.

An "antimicrobial peptide" (AmP) refers to oligo- or polypeptides that kill (i.e., bacteriocidal) or inhibit the growth of (i.e., bacteriostatic) microorganisms including bacteria, yeast, fungi, mycoplasma, viruses or virus infected cells, and/or protozoa. In some instances, AmPs have been reported to have anticancer activity. Generally, antimicrobial peptides are cationic molecules with spatially separated hydrophobic and charged regions. Exemplary antimicrobial peptides include linear peptides that form an α-helical structure in membranes or peptides that form β-sheet structures optionally stabilized with disulfide bridges in membranes. Representative antimicrobial peptides include, but are not limited to, cathelicidins, defensins, dermcidin, and more specifically magainin 2, protegrin, protegrin-1, melittin 11-37, dermaseptin 01, cecropin, caern, ovispirin, and alamethicin. Naturally occurring antimicrobial peptides include peptides from vertebrates and non-vertebrates, including plants, humans, fungi, microbes, and insects.

The terms "amino acid residue" and "peptide residue" refer to an amino acid or peptide molecule without the —OH of its carboxyl group (C-terminally linked) or the proton of its amino group (N-terminally linked). In general the abbreviations used herein for designating the amino acids and the protective groups are based on recommendations of the IUPAC-IUB Commission on Biochemical Nomenclature (see *Biochemistry* (1972) 11:1726-1732). Amino acid residues in peptides are abbreviated as follows: Alanine is Ala or A; Cysteine is Cys or C; Aspartic Acid is Asp or D; Glutamic Acid is Glu or E; Phenylalanine is Phe or F; Glycine is Gly or G; Histidine is His or H; Isoleucine is Ile or I; Lysine is Lys or K; Leucine is Leu or L; Methionine is Met or M; Asparagine is Asn or N; Proline is Pro or P; Glutamine is Gln or Q; Arginine is Arg or R; Serine is Ser or S; Threonine is Thr or T; Valine is Val or V; Tryptophan is Trp or W; and Tyrosine is Tyr or Y. Formylmethionine is abbreviated as fMet or fM. By the term "residue" is meant a radical derived from the corresponding α-amino acid by eliminating the OH portion of the carboxyl group and the H portion of the α-amino group. The term "amino acid side chain" is that part of an amino acid exclusive of the —CH(NH$_2$)COOH portion, as defined by K. D. Kopple, "Peptides and Amino Acids", W. A. Benjamin Inc., New York and Amsterdam, 1966, pages 2 and 33; examples of such side chains of the common amino acids are —CH$_2$CH$_2$SCH$_3$ (the side chain of methionine), —CH$_2$CH(CH$_3$)—CH$_2$CH$_3$ (the side chain of isoleucine), —CH$_2$CH(CH$_3$)$_2$ (the side chain of leucine) or —H (the side chain of glycine).

The term "non-naturally occurring amino acid" refers to any amino acid (defined based to the backbone as CH(NH$_2$)COOH), with a sidechain that does not correspond to a naturally occurring amino acids. Non-natural amino acids include any D-amino acids (described below), amino acids with sidechains that are not found in nature, and peptidomimetics. Examples of peptidomimetics include, but are not limited to, β-peptides, γ-peptides, and δ-peptides; oligomers having backbones which can adopt helical or sheet conformations, such as compounds having backbones utilizing bipyridine segments, compounds having backbones utilizing solvophobic interactions, compounds having backbones utilizing side chain interactions, compounds having backbones utilizing hydrogen bonding interactions, and compounds having backbones utilizing metal coordination.

All of the amino acids in the human body, except glycine, are either right-hand or left-hand versions of the same molecule, meaning that in some amino acids the positions of the carboxyl group and the R-group are switched. Nearly all of the amino acids occurring in nature are the left-hand versions of the molecules, or the L-forms. Right-hand versions (D-forms) are not found in the proteins of higher organisms, but they are present in some lower forms of life, such as in the cell walls of bacteria. They also are found in some antibiotics, among them, streptomycin, actinomycin, bacitracin, and tetracycline. These antibiotics can kill bacterial cells by interfering with the formation of proteins necessary for viability and reproduction.

The term "database" refers to a collection of information. The information is typically organized to facilitate access to the data. Typically databases are stored electronically, for example on a computer. Databases are available commercially as well as in the literature, or can be construed using appropriate search terms from information in the literature, for example, using the National Institutes of Health Medline. Exemplary databases for antimicrobial peptides include the University of Nebraska Medical Center Antimicrobial Peptide Database. Alternatively, other databases may be used such as the AMSdb, A. Tossi, Antimicrobial sequences database (AMSDb) (2002), which may be supplemented with additional peptides from Swiss-Prot/TrEMBL, A. Bairoch, R. Apweiler, *Nucleic Acids Research* 28, 45 (2002).

The term "grammar" refers to a rule or set of rules based on a pattern existing within a known database that describes the allowed arrangement(s) of specific sequences of amino acids. For example, [I/V/L]K[T/E/G/D/L]V[G/A]K[A/E/K/N/H][G/A]K (SEQ ID NO:1) is an exemplary grammar from which 600 non-naturally occurring antimicrobial peptide sequences can be produced. If only one letter is given for a position, that is the only allowed amino acid for the pattern. If a bracket is given, any of the letters within the bracket may be chosen at that position. The terms grouped in the bracket may be every amino acid that shows up instantiations of the grammar within natural AmPs. Alternatively, bracketed expressions may be functionally similar amino acids such as R and K, even if they do not both show up in natural instantiations. Grammars may also have wild card positions in which any amino acid may be chosen (including non-natural amino acids).

The term "wildcard" refers to a character within a grammar that is not specified. Within a grammar composed of amino acids, a wild card position can be replaced by any amino acid, natural or non-natural. In some applications, it may be desired to restrict wild-card to be replaced by only natural amino acids. The number of wildcards allowed within a specified window of amino acids within a grammar may be specified if desired.

The term "homology" means the fraction of amino acids in two sequences that are identical after alignment, including the insertion of gaps if necessary. Homology may be defined over different window sizes of amino acids. The term "similarity" may be understood to mean the fraction of amino acids in two sequences that are identical when grouping similar amino acids and after alignment, including the insertion of gaps if necessary. Grouping similar amino acids may include grouping functionally equivalent amino acids, such as positively charged amino acids. The determination of similar groupings will vary according to the application at hand, and any appropriate measure of homology may be employed. Optionally, and typically, homology may be determined using standard techniques known in the art, such as the Best Fit sequence program described by Devereux, et al., *Nucl. Acid Res.* 12:387-395 (1984), or the BLASTX program for the comparison of amino acid sequences (Altschul, et al., J. Mol. Biol., 215:403-410 (1990)). Groupings including non-natural amino acids could be created and used as appropriate based on the structure or functional characteristics of each amino acid. For grammars with bracketed expressions at some positions meaning multiple amino acids are acceptable, a position in a sequence is considered identical to the corresponding position in the grammar if the amino acid matches any of the amino acids in the bracketed expression. Both homology and similarity may be defined over a specified window size, if desired.

The term "highly conserved" refers to a nucleic acid or amino acid sequence that is shared between two or more kingdoms. A representative highly conserved gene is the gene encoding actin. Actin residues from amoebas and from animals are identical at 80 percent of the positions. In vertebrates, the four α-actin isoforms present in various muscle cells and the β- and γ-actin isoforms preset the non-muscle cells differ at only four or five positions. Thus, a highly conserved nucleic acid or polypeptide has about 80% or more sequence identity between two or more kingdoms. Sequences may have a higher degree of conservation, for example 85, 90, 92, 95, or 98% conserved. The term "conserved" refers to a nucleic acid or amino acid sequence that is shared between different species, for example, all mammals. Conserved can also refer to a shared order of genes on a chromosome.

The term "non-toxic" refers to a substance or compound that does not cause or contribute to a significant adverse effect or reaction in a biological organism. As measured in the examples, this is a peptide that does not induce a significant amount, i.e., no more than 50%, of hemolysis of red blood cells, and preferably less, when used at a therapeutic concentration. Preferably, 50% hemolysis is not achieved at 32 μg/ml. More preferably, 50% hemolysis is not achieved at 128 μg/ml. Most preferably, 50% hemolysis is not achieved at 512 μg/ml.

The term "cluster" refers to grouping members of a larger set into subgroups which each contain similar members. Clustering may be carried out by standard computation tools including K-means clustering, expectation maximization clustering, hierarchical clustering, and many others. The similarity may be based on the definition above of amino acids with similar functional or chemical properties, which perhaps may be determined by a blosum matrix. An alternative measurement of similarity must be selected for non-natural amino acids.

The term "mask" refers to removing portions of sequences from a database in order to perform additional pattern discovery in which those sequence fragments are not desired. This may be useful in pattern discovery if a first round of discovery is done to find patterns with few wild card positions. If additional pattern discovery is desired to find patterns with more wild cards and masking is not used, the variations of the previously, found patterns with few wild cards will dominate the discovery results. To prevent this, sequences conforming to the patterns in the first round of pattern discover are masked. This means going through the members of the database and replacing every instantiation of the pattern with a series of x's, so that when pattern discovery is rerun, these sequences are not present, i.e., the amino acid sequences that would lead to an overflow of patterns are removed or masked, so they are no longer in the database.

As used herein, "polypeptide", "peptide", and "oligopeptide" refers generally to peptides and proteins having more than about ten amino acids, most preferably more than 9 and less than 150, more preferably less than 100, most preferably 9-51. The polypeptides can be "exogenous," meaning that they are "heterologous," i.e., foreign to the host cell utilized, such as human polypeptide produced by a bacterial cell. Exogenous also refers to substances that are added from outside cells, not endogenous (produced by cells).

A peptide encompasses organic compounds composed of amino acids, whether natural or synthetic, and linked together chemically by peptide bonds. The peptide bond involves a single covalent link between the α-carboxyl (oxygen-bearing carbon) of one amino acid and the amino nitrogen of a second amino acid. Small peptides with fewer than about ten constituent amino acids are typically called oligopeptides, and peptides with more than ten amino acids are termed polypeptides. Compounds with molecular weights of more than 10,000 Daltons (50-100 amino acids) are usually termed proteins.

II. Methods

The systems and methods described herein include, among other things, systems and methods for designing peptides that have a desired characteristic or property, for example, the systems and methods described herein can be used to design peptides that have antimicrobial properties. In a first process, the methods include identifying a database of peptide sequences that are associated with the characteristic of interest. For example, a database of peptides may be identified whose members have antiviral properties, wound response properties, antimicrobial (antibacterial, antifungal, antiviral, anti-protozoa) properties or some other property of interest. Once the database is identified, the database may be processed in a pattern recognition procedure that identifies a set of patterns that is representative of a peptide having, the characteristic of interest.

A. Databases

The process described herein is effective with respect to analysis of databases that are publicly available. There are a variety of sources of such peptides. In the preferred embodiment, the database contains the sequences of gene encoded antimicrobial peptides and proteins. It may also include, when available, the sequences of precursors and of putative antimicrobial peptides as deduced from DNA sequencing. Typically, the available databases are oriented towards peptides of animal and plant sequences, although peptides and proteins of bacterial origin may be included. One database is the AMSDb that is correlated to the SWISS-PROT protein sequences database. That database has recently been updated and maintained within the framework of the European "PANAD" (Peptides As Novel Antiinfective Drugs) Project (European 5th framework programme, project N° QLK2-CT-2000-00411).

The database employed will depend upon the specifies of the application. For example, it may be that the system is directed to design AmPs for plants, and as such the pattern analysis performed by the pattern recognition processor may only process AmPs for plants and the database will be limited to AmPs associated only with plants. Additionally, databases may be developed that are directed to AmPs having a particular mechanism of action. For example, AmPs generally disrupt the membranes of a target cell, causing lysis of the cell. How this occurs may vary, and recently, several peptides with unusual folds that have strong antimicrobial activity have been identified, and their solution structure determined by NMR. The pattern recognition process 12 is employed to find a grammar for AmPs having this particular feature. Alternatively, patterns may be identified that the system uses to eliminate candidate sequences. In either case, the database selected may be chosen by one of skill in the art such that the data studied and processed is suited to the task.

B. Systems for Selection of Grammars and Derivation of Peptides

The systems and methods described above provide for a comprehensive analysis of the sequence that may lead to a desired characteristic behavior. These systems and methods may process a substantial volume of sequence data, as well as carry out a substantial number of repetitive operations and calculations. Automated tools for processing the data are desirable. The systems and methods lend themselves well to automation, at least for portions of the process. One such automated system is depicted as a functional block diagram in FIG. 1. FIG. 1 depicts a system 10 that includes a pattern recognition processor 12, a sequence design processor 14, a database of sequence data 16 and a data file 18 having the designed sequences, such as peptide sequences, thereon. The system 10 depicted in FIG. 1 will typically be implemented as a computer program operating on one or more conventional data processing platforms, such as an IBM PC-compatible computer running the Windows operating systems, or a SUN workstation running a Unix operating system. Alternatively, the data processing system can comprise a dedicated processing system that includes an embedded programmable data processing system. For example, the data processing system can comprise a single board computer system that has been integrated into a system for performing peptide design process. The system 10 may be a dedicated piece of laboratory equipment. In either of these cases, the system 10 will be understood as a computer program that directs the operation of a data processing platform to configure the platform into the system 10 depicted in FIG. 1. The system may also be understood to include computer readable media having stored thereon instructions for operating a data processing system to carry out the functions and operations described herein.

In one embodiment the pattern recognition processor 12 is a software module that executes on the data processing platform to direct the platform to collect sequence data from the database 16, and process that data to recognize patterns that occur within the sequences. An exemplary process using the Teiresias pattern discovery process is described more fully below. The depicted database 16 may be any suitable database system, including the commercially available Microsoft Access database, and may be a local, remote or a distributed database system. The design and development of suitable database systems are described in McGovern et al., A Guide To Sybase and SQL Server, Addison-Wesley (1993). The database 16 may be supported by any suitable persistent data memory, such as a hard disk drive, RAID system, tape drive system, floppy diskette, or any other suitable system. In certain embodiments, the database 16 is substantially remote from the pattern recognition processor 12, and a network connection is employed to provide access to the data stored in the database.

The pattern detection systems and the described evolutionary candidate peptide production processes described above may be realized as software processes that were designed and developed from principles known in the art of computer programming, including those set forth in Wall et al., Programming Perl, O'Reilly & Associates (1996); and Johnson et al, Linux Application Development, Addison-Wesley, (1998). FIG. 1 further depicts the process as including a server. The server may be a conventional data processing platform such as an IBM PC-compatible computer running the Windows operating systems, or a SUN workstation running a Unix operating system. Alternatively, the data processing system can comprise a dedicated processing system that includes an embedded programmable data processing system. For example, the data processing system can comprise a single board computer system that has been integrated into a system for performing peptide design process. The peptide design systems can be realized as a software component operating on a conventional data processing system such as a Unix workstation. In that embodiment, the peptide design system can be implemented as a C language computer program, or a computer program written in any high level language including C++, Fortran, Java or basic.

In an embodiment where microcontrollers or DSPs are employed, the peptide design system can be realized as a computer program written in microcode or written in a high level language and compiled down to microcode that can be executed on the platform employed. The development of such peptide design system is known to those of skill in the art, and such techniques are set forth in Digital Signal Processing Applications with the TMS320 Family, Volumes I, II, and III, Texas Instruments (1990). Additionally, general techniques for high level programming are known, and set forth in, for example, Stephen G. Kochan, Programming in C, Hayden Publishing (1983). It is noted that DSPs are particularly suited for implementing signal processing functions, including preprocessing functions such as image enhancement through adjustments in contrast, edge definition and brightness. Developing code for the DSP and microcontroller systems follows from principles well known in the art.

The discussed databases can be any suitable database system, including the commercially available Microsoft Access database, and can be a local or distributed database system. The design and development of suitable database systems are described in McGovern et al., A Guide To Sybase and SQL Server, Addison-Wesley (1993). The database can be supported by any suitable persistent data memory, such as a hard disk drive, RAID system, tape drive system, floppy diskette, or any other suitable system.

The systems and methods may be employed for designing any type of peptide or protein. For purposes of clarity, the system 10 is described with reference to an exemplary process for generating antimicrobial peptides of the type that may be effective as antibiotic therapies.

C. Grammars

Antimicrobial peptides (AmPs) are small proteins used by the innate immune system to attack and kill bacteria, J. Rolff, T. Siva-Jothy, Science 301, 472 (2003), D. A. Kimbrell, B. Beutler, Nat Rev Genet 2, 256 (2001). These peptides are ubiquitous among multicellular eukaryotes and have been found in diverse contexts including frog skin, M. Simmaco, G. Mignogna, D. Barra, Biopolymers 47, 435 (1999), scorpion venom, L. Moerman, et al., European Journal of Biochemistry 269, 4799 (2002), and human sweat, B. Schiettek, et al., Nature Immunology 2, 1133 (2001). Preliminary studies of AmPs indicate that their amphipathic structure gives rise to a modularity among AmP sequences. The repeated usage of sequence modules—which may be a relic of evolutionary divergence and radiation—may be analogized to the use of words and phrases in a natural language, such as English. For example, the pattern QxEAGxLxKxxK (SEQ ID NO:2) (the ".x" means that any amino acid will suffice) is present in over 90% of cecropins, an AmP common in insects.

Based, at least in part, on this observation, the systems and methods described herein model the AmP sequences as a formal language over the set of amino acids, D. Jurafsy, J. H. Martin, Speech and Language Processing: An Introduction to Natural Language Processing, Computational Linguistics, and Speech Recognition (Prentice Hall, Upper Saddle River, N.J., 2000).

This language can be generated by a set of right-linear grammars, such as th ceropin grammar above. Right-linear grammars—also known as regular grammars or regular expressions—are simple rules that describe allowed arrangements of characters, N. Chomsky, *IRE Transactions on Information Theory* 2, 113 (1956). These grammars are useful for modeling short-range dependencies in primary sequences and are commonly used to represent motifs or patterns, D. B. Searls, *Nature* 420, 211 (2002), D. B. Searls, *Artificial Intelligence and Molecular Biology*, L. Hunter, ed. (AAAI Press, 1992), pp 47-120.

Initial Selection of Grammars

To elucidate the grammar of AmPs, any pattern recognition process may be employed. A pattern discovery tool may be applied to a database to determine some or all patterns that exist within the database including semi-conserved or fully conserved patterns. This could include the programs GEMODA, Teiresias, Gibbs Sampler (Lawrence C E, Altschul S F, Boguski M S, Liu J S, Neuwald A F, Wootton J C. Detecting subtle sequence signals: a Gibbs sampling strategy for multiple alignment. Science, 1993 Oct. 8; 262(5131):208-14.), and MEME (Bailey T L, Elkan C. Fitting a mixture model by expectation maximization to discover motifs in biopolymers. Proc Int Conf Intell Syst Mol Biol. 1994; 2:28-36.). Pattern discovery may be carried out with or without functionally equivalent groups defined, depending on the pattern discovery tool used.

Teiresias (see, I. Rigoutsos, A Floratos, *Bioinformatics* 14, 55 (1998)) for a detailed description of the Teiresias algorithm) was used for pattern analysis as described in the examples. Given a formal language, Teiresias enumerates right-linear grammars that are maximal in both composition and length. Using Teiresias, the methods described herein were used as described in the following example to identify an exhaustive set of approximately 684 regular grammars in the set of known eukaryotic AmP sequences. These sequences consisted of approximately 526 AmPs from the University of Nebraska Medical Center Antimicrobial Peptide Database. Other databases could be used, such as the AMSdb, A. Tossi, Antimicrobial sequences database (AMSDb) (2002), which may be supplemented with an additional approximately 200 antimicrobial peptides from Swiss-Prot/TrEMBL, A. Bairoch, R. Apweiler, *Nucleic Acids Research* 28, 45 (2002) that were not included in AMSdb.

Alternatively, these pattern discovery tools can be applied to a database with other common properties or functions, including non-toxicity, wound response, signaling, anti-cancer activity, antiviral activity, etc. Alternatively, the pattern discovery tools can be applied to a database that has more than one property of interest, for example, antimicrobial and non-toxic.

TEIRESIAS finds patterns that are a subset of regular languages, the simplest class of languages on the Chomsky linguistic hierarchy. These patterns are "grammars", which are formulated as regular expressions. These expressions are capable of modeling relatively small sequence structures, such as a protein-binding motif, but fail in the modeling of structures with higher-order dependencies, such as a hairpin loop of RNA. In general, TEIRESIAS can be applied to the discovery of patterns in any type of character sequences, whether amino acids, nucleotides, or discrete numbers. Given a set of input character sequences and a set of integer parameters L, W, and K, TEIRESIAS will find all patterns having at least L non-wildcard characters over a span of any W characters and occurring at least K times among the input sequences. In essence. L/W reflects a minimum "density" of non-wildcard characters in the pattern, while L reflects the minimum pattern length. Any pattern longer than L must meet the L/W criterion for any given window of W consecutive characters. Preferably L is five to ten amino acids, most preferably 6 to 8; L/W is 0.3 to 1.0, most preferably 0.5 to 1.0; and K is two to eight, most preferably two to five.

TEIRESIAS returns a list of patterns, the number of occurrences of those patterns, the number of different sequences in which the patterns occur, and (optionally) "offset lists" indicating the location of each pattern occurrence. The noteworthy aspect of TEIRESIAS is the way by which it obtains these results. Rather than searching for and enumerating every single possible pattern or n-mer, it only initially enumerates "elementary" patterns; that is, only those patterns satisfying the L/W constraint that have exactly L non-wildcard characters are enumerated. Longer patterns are then created by "convolution", which allows for elementary patterns to be combined provided that there is sufficient support and overlap between them. This strategy eliminates a great deal of computation time when compared to other brute force methods. As a result of this approach to discovering patterns, the algorithm can claim the following three important properties:

All maximal patterns are reported

Only the maximal patterns are reported

Running time is quasi-linearly dependent upon the output (the number of patterns present in the data).

The consequence of the first and second properties is that a complete, non-redundant set of patterns is returned for a given set of parameters. Such a pattern-space search is thus exhaustive, and it is certain that given the parameters supplied to TEIRESIAS, all qualifying patterns have been discovered. This strategy is more desirable than the results of some other efforts at pattern discovery, which use a priori ideas of the characters composing the patterns or ad hoc methods to find patterns. The impact of the third property is that patterns of any length can be discovered. Since computation time is only output-dependent, no restrictions are placed on the maximum pattern length as is done in some other routines to make problems tractable.

Teiresias outputs its grammars in regular expression format, using wildcards. In the preferred method, the wildcards in the grammars are replaced with a bracketed expression containing the set of amino acids implied by the offset list of the grammar.

Optionally, one may de-reference each wildcard in the grammars to a bracketed expression. That is, replace each wildcard with the set of amino acids implied by the grammar's offset list. Optionally, the grammars may be cut to a specified size such as 10 amino acids using a sliding window.

Selectivity filters may be applied by comparing the derived grammars to a database having the property of interest and comparing it to a larger database not known to represent the property of interest. A specificity filter may be used which eliminates a grammar which does not occur in the database with the property of interest more than a certain fraction of the time relative to the grammars occurrences in the non-specific database. Optionally, the grammar will be maintained only if 80% of the total occurrences across both the database of interest and the uncharacterised database are within the database of interest.

Figures 2A, 2B:
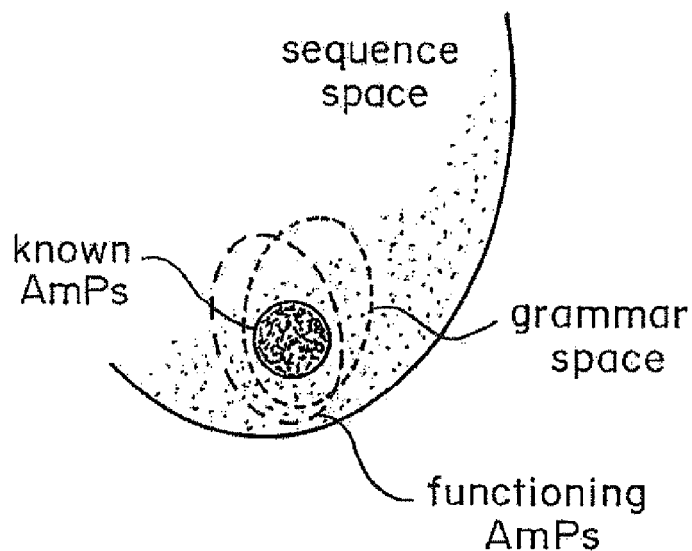
FIGS. 2A and 2B depict an example of a peptide design space and an example of a designed sequence along with 2 grammars that occur within the designed sequence. Using the methods described in this example, there grammars that occur in the designed sequence starting at every amino acid position from 1 to 11. Only 2 of these 11 grammars are shown for the sake of clarity.
Figure 3:
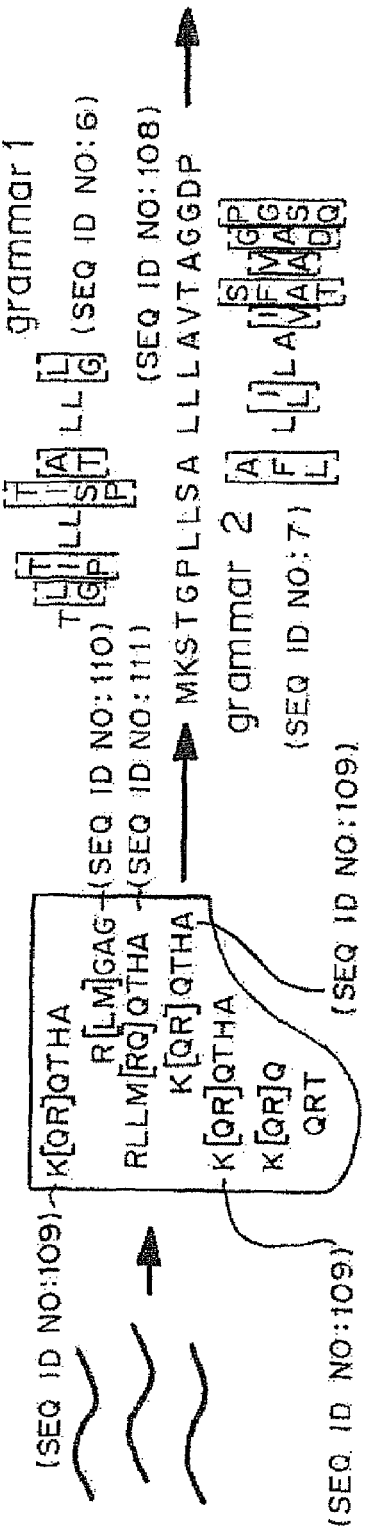
FIG. 3 depicts pictorially a schematic of the in silico pattern discovery and tiling employed by the process.
Figure 3:
Figure 3:

This process is depicted in FIG. 2B. More particularly, FIGS. 2A and 2B depict a peptide design space (FIG. 2A), and an example of a scoring process for generating a measure of the fraction of a sequence that is covered by identified patterns or grammars (FIG. 2B). In particular, FIG. 2A depicts a space diagram 20 that includes the sequence space 22 representative of the space that contains all possible sequences for a peptide of a particular length. The "sequence space" 22 is the combinatorially large set of all possible sequences. Even for a 20 amino acid peptide this base is large: on the order of $10^{26}$ power of sequences. It further depicts a grammar space 24 representative of the portion of possible sequences that comply with the grammar, and a functioning AmP space 26 representative of the portion of the total sequence space that contains a sequence representative of a peptide that has an anti-microbial function. It will be noted that in FIG. 2A, the grammar space 24 and the functioning AmP space 26, are shown to diverge. This represents the understanding that not all sequences that are grammatical will provide a functioning AmP, and similarly, not all functioning AmPs will be grammatical, in that they comply with the grammars determined in this process. Such divergence is possible and likely, although not necessary. The depicted divergence indicates that in one practice, a plurality of candidate AmPs are created through the processes described herein, but each candidate AmP may not ultimately have the desired biological activity. FIG. 2A further depicts the sequence space 28 defining the set of naturally occurring peptides that have the characteristic of interest. As will be described below, the peptide design process may optionally filter out from the pool of query sequences, those sequences that are known to occur naturally.

The linguistic model focuses the search base to the grammar space 24 but allows a deviation from natural peptide sequences. This allows the system 10 to be employed to design peptides that show no significant or virtually no significant homology to any naturally occurring sequences, but have the desired function.

FIG. 2B shows an example of a synthesized sequence. Above and below the subsequence are grammars that match the sequence in a tiled arrangement. For each bracketed expression any of the amino acids listed in the bracket will suffice. FIG. 2B depicts a grammar 1. The example grammar derived using the pattern recognition process discussed above includes a sequence of 10 amino acids. The grammar 1 has a number of optional expressions. For example, the second value of sequence may be either L or G. Similarly the third value of the sequence may be T, I or P. The first value of the sequence is T. Grammar 2 is expressed using a similar notation. Based on the tiling method discussed below, there would be a 10 amino acid grammar starting at the first 11 amino acid positions. Only 2 matching grammars are shown for clarity.

In one alternate embodiment, the method may begin with combinatorially enumerating all or substantially all grammatical sequences based on a given set of grammars that may be representative of a peptide having a characteristic of interest.

An example of one embodiment of the method produces an AmP grammar described by a sequence [IVL]K[TEGDK]V [GA]K[AELNH][VA][GA]K (SEQ ID NO:3). As a first step, one can enumerate all or substantially all possible sequences conforming to this grammar. For each grammar sequence one may choose one amino acid for each bracketed position limited to the amino acids within brackets for that corresponding position. In this example, one may choose one of either I, V or L for the first position and follow a similar procedure for each of the other bracketed positions. In this particular example, one has the option of choosing one amino acid among each of three amino acids in the first position, five amino acids in the third position, two amino acids in the fifth position, five amino acids in the seventh position, two amino acids in the eighth position and two amino acids in the ninth position. One may list all sequences of length ten comprising different combinations of amino acids by multiplying out the number of possible amino acids for each bracketed position giving us 3×5×2×5×2×2=600 sequences.

Secondary Selection of Grammars

Sequences showing a relatively high degree of similarity to the naturally occurring sequences may then be removed if a desired outcome of the design is to increase the diversity of sequences with the desired property well beyond those known in the database. This may be done by measuring the homology or similarity of each sequence to all members of the database of sequences with a desired property. Optionally, any sequence with greater than 85% homology to a sequence in the database may be removed. More preferably, any sequence with greater than 70% homology to a sequence in the database may be removed. Alternatively, any designed sequence with more that a specified number of characters in common with a natural sequence may be removed. Optionally, any designed sequence with more than three characters in common with a natural sequence may be removed. More preferably, any designed sequence with more than five characters in common with a natural sequence may be removed.

A variety of scoring procedures may be used to determine how well a designed sequence is covered by grammars. In one method, the score is the fraction of amino acids in a designed sequence that have identity with at least one grammar. In an alternate practice, the score is the fraction of amino acids in a designed sequence that has homology to at least one grammar. In an optional practice, grammars that have been shown to be highly indicative of the characteristic of interest may be weighted more heavily than other sequences. This may be based on testing the degree to which each member of the database has the characteristic of interest (e.g., some activity), and assigning a weight to each grammar based on the activities of the members of the database that are matched by that grammar. In one practice, the score of the designed sequence would be the product of the percentage of the sequence covered by grammars and the average weight of the grammar based on database activity.

For some design methods, it may be enforced that the entire designed designed sequence is covered by grammars. In this case, designed sequences may be weighted based on the importance of each grammar that occurs. In one practice, a score is developed by weighting the grammars based on the frequency with which they appear in the database. This score is computed by making a sequence dot plot matrix (Maizel et al, Poc Natl Acad Sci USA 78, 7665-7669, 1981). In a dot plot, columns may represent positions of the sequence being evaluated and the rows may represent concatenated sequences of naturally occurring AmPs. A dot may be placed in the matrix wherever a grammar matches or substantially matches both a naturally occurring AmP and the sequences being evaluated. The score may be computed by counting the total number of dots in the matrix.

In other embodiments, the systems and methods described herein allow for using a scoring function that considers two or more grammars generated from different and respective pattern recognition processes. For example, the scoring function may score a sequence based on the inclusion within the sequence of one or more patterns that are associated with a first characteristic, such as being antimicrobial, and the inclusion within the sequence of a pattern associated with a second characteristic, such as being anti-toxic. In this way, the processes described herein may have nested criteria to allow for the development of biological sequences that are designed to exhibit two or more desirable characteristics.

Linguistic strategies, like the grammar-based approach used here, can lead to the design of many peptides, not just AmPs. The benefit of considering a large number of newly generated peptide sequences to include all or substantially all sequences of a desired length that conform to at least one of the set of grammars is to help increase the number of highly scored candidate sequences. Also, the degree to which the designed sequence may be matched by grammars seem to correlate with antimicrobial activity. Additionally, the systems and methods described herein may be employed to generate peptides that have multiple desired characteristics. For example, the systems and methods described herein may be extended to take into consideration a second or third characteristics, such as the hemolytic characteristic of a peptide. To this end, and as described above, patterns such as grammars, may be generated and used to design peptides having these second and third characteristics. Of the candidate sequences generated, the systems and methods described herein may apply these new patterns to the candidate sequences to identify sequences that meet both criteria, and therefore provide both properties.

D. Creation of Peptide Database

The proteins and peptides processed and designed by the systems and methods described herein may be derived using databases from any organism, including prokaryotes and eukaryotes, with enzymes from bacteria, fungi, extremeophiles such as the archebacteria, insects, fish, animals (particularly mammals and particularly human) and birds. Although described with reference to antimicrobial peptides, suitable proteins include, but are not limited to, industrial and pharmaceutical proteins, including ligands, cell surface receptors, antigens, antibodies, cytokines, hormones, neuropeptides, signaling peptides, and enzymes. Suitable classes of enzymes include, but are not limited to, hydrolases such as proteases, carbohydrates, lipases; isomerases such as racemases, epimerases, tautomerases, or mutases; transferases, kinases, oxidoreductases, and phophatases. Suitable enzymes are listed in the Swiss-Prot enzyme database. Suitable peptide classes include antimicrobial peptides, antiviral peptides, anticancer peptides, signaling peptide, etc.

Specifically included within "protein" are fragments and domains of known proteins, including functional domains such as enzymatic domains, binding domains, etc., and smaller fragments such as turns, loops, etc. That is, portions of proteins may be used as well.

The proteins or peptides may be designed to have additional features and characteristics. For example, they may be more stable than the known peptides that were used as the starting point. Stable may mean that the new protein retains either biological activity or conformation past the point at which the parent molecule did. Stability includes, but is not limited to, thermal stability, i.e. an increase in the temperature at which reversible or irreversible denaturing starts to occur; proteolytic stability, i.e. a decrease in the amount of protein which is irreversibly cleaved in the presence of a particular protease (including autolysis; stability to alterations in pH or oxidative conditions; chelator stability; stability to metal ions; stability to solvents such as organic solvents, surfactants, formulation chemicals, etc. Peptides may also be specifically designed to retain antimicrobial activity when covalently tethered to a surface.

In a preferred embodiment, the designed proteins are chemically synthesized as is known in the art. Laboratory synthesis of peptides has risen to the level of a well-defined art in recent years. Synthetic peptides, composed of as many as a hundred amino acids in specified sequence, have been prepared in the laboratory with good purity and high yields. In organic chemistry, peptide synthesis is the creation of peptides, which are organic compounds in which more than two amino acids bind via peptide bonds. Peptides are synthesized by combining the carboxyl group of one amino acid with the amino group of another. During peptide synthesis, one side of the amino acids has to be protected to keep the acids from reacting with themselves. There are two conventional types of in methods for obtaining polypeptides. One is the stepwise elongation method, in which the amino acids are connected step-by-step in turn. The other is the fragment condensation method, in which peptide fragments are coupled to each other. Although the former can elongate the peptide chain without racemization, the yield drops if only condensation is used. Fragment condensation is better than stepwise elongation for synthesizing sophisticated long peptides, but its use must be restricted in order to protect the racemization. There are two conventional ways of synthesizing polypeptides. One is liquid-phase peptide synthesis, and the other is solid-phase peptide synthesis. When the former is utilized, the product can usually be purified halfway, yet time, effort, skill, and experience are necessary. When the latter is used, less time and effort are necessary for the synthesis because the experimental operation is simpler, but it is impossible to purify the peptide during the process.

The choice of which method to use is left to the person who synthesizes the peptide. The established practices for peptide synthesis are particularly useful when the designed proteins are short preferably less than 150 amino acids in length, with less than 100 amino acids being preferred, and between 9 and 51 amino acids being particularly preferred, although as is known in the art, longer proteins can be made chemically or enzymatically. In the most preferred embodiment, at least 70% homology or similarity to a grammatical sequence is particularly preferred. Chemical synthesis allows the inclusion of unnatural amino acids. These unnatural amino acids can be incorporated into designs either randomly or by substituting them for the natural amino acids to which they are most similar. As databases are enlarged to include sequences which include unnatural amino acids, the non-natural amino acids may be treated as additional letter choices beyond the 20 natural amino acids and the same pattern discovery tools may be applied with a larger alphabet. One method to begin to include D-amino acids would be to allow their substitution for their L-amino acid counterparts. D-amino acids would be particularly useful to replace a stretch of L-amino acids known to be susceptible to proteases.

In an optional practice, particularly for longer proteins or proteins for which large samples are desired, the optimized sequence is used to create a nucleic acid such as DNA which encodes the optimized sequence and which can then be cloned into a host cell and expressed. Thus, nucleic acids, and particularly DNA, can be made which encodes each optimized protein sequence. This is done using well known procedures. The choice of codons, suitable expression vectors and suitable host cells will vary depending on a number of factors, and can be easily, optimized as needed. In another optional practice the peptide sequences may be synthesized using in vitro translation from DNA sequences.

Once made, the designed proteins and peptides may be experimentally evaluated and tested for structure, function and stability, as required, using methods known to those skilled in the art.

Examples of useful peptides having antimicrobial activity are shown in the examples.

The peptides can be provided in solution, suspension, or immobilized, as discussed below. The peptides may, be chemically modified, for example, by pegylation using commercially available reagents and methods, in order to prolong in vivo half-life and inhibit uptake by the reticuloendothelial system (RES). The peptides can be coupled to a substrate or fused to one or more other proteins, lipids, or compounds.

III. Products and Applications Thereof

The systems and methods described above are generally useful for the creation of one or more grammars based on specific databases of peptides and/or proteins having desirable feature(s), such as antimicrobial activity. These grammars are used for the design of a database of peptides with one or more of the desirable activities.

In a particular application, the systems and methods described herein have been employed for synthesizing antimicrobial peptides. Peptides may be employed in medicine, for example, for treating cancer or diabetes, for industrial applications, such as for antimicrobial agents in paints, peptide toxins for insecticides, or for any other application. These may be formulated for systemic, local, or regional delivery, via oral, injection, topical, or mucosal administration. The pharmaceutical formulations can provide immediate, delayed, pulsed, or a combination of release profiles. The peptides can also be adsorbed or coupled to substrates including medical devices, medical drapes and wound dressing, both woven and non-woven, natural and synthetic polymers, and implants. Alternatively, the peptides can be utilized in industrial applications such as in paint, wall coverings, in filters, coatings for household and medical furniture, equipment, and supplies (e.g. countertops, pots and pans, refrigerators, scalpels, needles, etc.)

A. Pharmaceutical Formulations

Peptides preferably have antimicrobial activity in the absence of significant toxicity. For implantation, peptides should not elicit an inflammatory response or promote encapsulation. Mixtures of peptides may be used to decrease the likelihood of resistance developing.

The peptides identified using the claimed system can be formulated for use as pharmaceutical compositions or applied to substrates, as discussed above. Peptides which are formulated are those having efficacy in an assay for antimicrobial activity, or other activity to be screened for, then tested for toxicity, and those having an appropriate therapeutic index formulated using standard techniques and excipients, for example, as tablets, capsules, powders, ointments, creams, sprays, solutions, suspensions, or other dosage forms.

"Immediate Release" or "IR" means the therapeutic pharmaceutical composition is provided in a formulation allowing the active agent to begin acting in a therapeutic manner substantially as soon as the agent becomes available in the body and/or bloodstream of the patient. A "delayed release dosage form" is one that releases a drug (or drugs) at a time other than promptly after administration. An "extended release dosage form" is one that allows at least a twofold reduction in dosing frequency as compared to that drug presented as a conventional dosage form (e.g. as a solution or prompt drug-releasing, conventional solid dosage form). A "modified release dosage form" is one for which the drug release characteristics, time course and/or location are chosen to accomplish therapeutic or convenience objectives not offered by conventional dosage forms such as solutions, ointments, or promptly dissolving dosage forms. Delayed release and extended release dosage forms and their combinations are types of modified release dosage forms. Pulsed release" refers to an initial release of drug, followed by a period of substantially no release, then more than one additional release of drug separated by a period of substantially no release. This does not mean that there are no blood levels of drugs between periods of release. "Sustained release" or "SR" means the therapeutic pharmaceutical composition is provided in a formulation such that the composition provides an initial therapeutic effect and also an ongoing or additional release of the therapeutic pharmaceutical composition or therapeutic effect over a desired period of time.

Matrix forming materials are materials which form strong, viscous gels upon hydration and provide control of drug diffusion and release. In hydrophilic matrix systems, matrix forming materials are uniformly incorporated throughout the tablet. Upon contact with water, the outer tablet layer is partially hydrated, forming a gel layer. The rate of diffusion of the drug(s) out of the gel layer and the rate of erosion of the gel layer determine overall tablet dissolution and drug delivery rates. Examples of matrix forming materials include cellulose ethers that are water-soluble such as methylcellulose, ethyl cellulose and hydroxypropyl methylcellulose.

Formulations are prepared using a pharmaceutically acceptable "carrier" composed of materials that are considered safe and effective and may be administered to an individual without causing undesirable biological side effects or unwanted interactions. The "carrier" is all components present in the pharmaceutical formulation other than the active ingredient or ingredients. The term "carrier" includes but is not limited to diluents, binders, lubricants, disintegrators, fillers, matrix-forming compositions and coating compositions.

"Carrier" also includes all components of the coating composition which may include plasticizers, pigments, colorants, stabilizing agents, and glidants. The delayed release dosage formulations may be prepared as described in references such as "Pharmaceutical dosage form tablets", eds. Liberman et. al. (New York, Marcel Dekker, Inc., 1989). "Remington—The science and practice of pharmacy", 20th ed., Lippincott Williams & Wilkins, Baltimore, Md., 2000, and "Pharmaceutical dosage forms and drug delivery systems", 6th Edition, Ansel et. al., (Media, Pa.: Williams and Wilkins, 1995) which provides information on carriers, materials, equipment and processes for preparing tablets and capsules and delayed release dosage forms of tablets, capsules, and granules.

Examples of suitable coating materials include, but are not limited to, cellulose polymers such as cellulose acetate phthalate, hydroxypropyl cellulose, hydroxypropyl methylcellulose, hydroxypropyl methylcellulose phthalate and hydroxypropyl methylcellulose acetate succinate; polyvinyl acetate phthalate, acrylic acid polymers and copolymers, and methacrylic resins that are commercially available under the trade name Eudragit™ (Roth Pharma, Westerstadt, Germany), Zein, shellac, and polysaccharides. Additionally, the coating material may contain conventional carriers such as plasticizers, pigments, colorants, glidants, stabilization agents, pore formers and surfactants. Optional pharmaceutically acceptable excipients present in the drug-containing tablets, beads, granules or particles include, but are not limited to, diluents, binders, lubricants, disintegrants, colorants, stabilizers, and surfactants.

Diluents, also termed "fillers," are typically necessary to increase the bulk of a solid dosage form so that a practical size is provided for compression of tablets or formation of beads and granules. Suitable diluents include, but are not limited to, dicalcium phosphate dihydrate, calcium sulfate, lactose, sucrose, mannitol, sorbitol, cellulose, microcrystalline cellulose, kaolin, sodium chloride, dry starch, hydrolyzed starches, pre-gelatinized starch, silicone dioxide, titanium oxide, magnesium aluminum silicate and powder sugar.

Binders are used to impart cohesive qualities to a solid dosage formulation, and thus ensure that a tablet or bead or granule remains intact after the formation of the dosage forms. Suitable binder materials include, but are not limited to, starch, pre-gelatinized starch, gelatin, sugars (including sucrose, glucose, dextrose, lactose and sorbitol), polyethylene glycol, waxes, natural and synthetic gums such as acacia, tragacanth, sodium alginate, cellulose, including hydroxypropylmethylcellulose, hydroxypropylcellulose, ethylcellulose, and veegum, and synthetic polymers such as acrylic acid and methacrylic acid copolymers, methacrylic acid copolymers, methyl methacrylate copolymers, aminoalkyl methacrylate copolymers, polyacrylic acid/polymethacrylic acid and polyvinylpyrrolidone. Some of the materials which are suitable as binders can also be used as matrix-forming materials such as hydroxypropyl methyl cellulose, ethyl cellulose, and microcrystalline cellulose.

Lubricants are used to facilitate tablet manufacture. Examples of suitable lubricants include, but are not limited to, magnesium stearate, calcium stearate, stearic acid, glycerol behenate, polyethylene glycol, talc, and mineral oil.

Disintegrants are used to facilitate dosage form disintegration or "breakup" after administration, and generally include, but are not limited to, starch, sodium starch glycolate, sodium carboxymethyl starch, sodium carboxymethylcellulose, hydroxypropyl cellulose, pre-gelatinized starch, clays, cellulose, alginine, gums or cross linked polymers, such as cross-linked PVP (Polyplasdone™ XL from GAF Chemical Corp).

Stabilizers are used to inhibit or retard drug decomposition reactions which include, by way of example, oxidative reactions.

Surfactants may be anionic, cationic, amphoteric or nonionic surface active agents. Suitable anionic surfactants include, but are not limited to, those containing carboxylate, sulfonate and sulfate ions. Examples of anionic surfactants include sodium, potassium, ammonium salts of long chain alkyl sulfonates and alkyl aryl sulfonates such as sodium dodecylbenzene sulfonate; dialkyl sodium sulfosuccinates, such as sodium dodecylbenzene sulfonate; dialkyl sodium sulfosuccinates, such as sodium bis-(2-ethylthioxyl)-sulfosuccinate; and alkyl sulfates such as sodium lauryl sulfate. Cationic surfactants include, but are not limited to, quaternary ammonium compounds such as benzalkonium chloride, benzethonium chloride, cetrimonium bromide, stearyl dimethylbenzyl ammonium chloride, polyoxyethylene and coconut amine. Examples of nonionic surfactants include ethylene glycol in monostearate, propylene glycol myristate, glyceryl monostearate, glyceryl stearate, polyglyceryl-4-oleate, sorbitan acylate, sucrose acylate, PEG-150 laurate, PEG-400 monolaurate, polyoxyethylene monolaurate, polysorbates, polyoxyethylene octylphenylether, PEG-1000 cetyl ether, polyoxyethylene tridecyl ether, polypropylene glycol butyl ether, Poloxamer™ 401, stearoyl monoisopropanolamide, and polyoxyethylene hydrogenated tallow amide. Examples of amphoteric surfactants include sodium N-dodecyl-â-alanine, sodium N-lauryl-â-iminodipropionate, myristoamphoacetate, lauryl betaine and lauryl sulfobetaine.

If desired, the tablets, beads, granules or particles may also contain minor amount of nontoxic auxiliary substances such as wetting or emulsifying agents, dyes, pH buffering agents, and preservatives.

Extended release formulations are generally prepared as diffusion or osmotic systems, for example, as described "Remington—The science and practice of pharmacy" (20th ed., Lippincott Williams & Wilkins, Baltimore, Md., 2000). A diffusion system typically consists of two types of devices, a reservoir and a matrix, and is well known and described in the art. The matrix devices are generally prepared by compressing the drug with a slowly dissolving polymer carrier into a tablet form. The three major types of materials used in the preparation of matrix devices are insoluble plastics, hydrophilic polymers, and fatty, compounds. Plastic matrices include methyl acrylate-methyl methacrylate, polyvinyl chloride, and polyethylene. Hydrophilic polymers include cellulosic polymers such as methyl and ethyl cellulose, hydroxyalkylcelluloses such as hydroxypropyl-cellulose, hydroxypropylmethylcellulose, sodium carboxymethylcellulose, and Carbopol™ 934, polyethylene oxides and mixtures thereof. Fatty compounds include, but are not limited to, various waxes such as carnauba wax and glyceryl tristearate and wax-type substances including hydrogenated castor oil or hydrogenated vegetable oil, or mixtures thereof. In certain embodiments, the plastic material is a pharmaceutically acceptable acrylic polymer, including but not limited to, acrylic acid and methacrylic acid copolymers, methyl methacrylate, methyl methacrylate copolymers, ethoxyethyl methacrylates, cyanoethyl methacrylate, aminoalkyl methacrylate copolymer, poly(acrylic acid), poly(methacrylic acid), methacrylic acid alkylamine copolymer poly(methyl methacrylate), poly(methacrylic acid) (anhydride), polymethacrylate, polyacrylamide, poly(methacrylic acid anhydride), and glycidyl methacrylate copolymers. In certain embodiments, the acrylic polymer is comprised of one or more ammonio methacrylate copolymers. Ammonio methacrylate copolymers are well known in the art, and are described in NF XVII as fully polymerized copolymers of acrylic and methacrylic acid esters with a low content of quaternary ammonium groups.

Alternatively, extended release formulations can be prepared using osmotic systems or by applying a semi-permeable coating to the dosage form. In the latter case, the desired drug release profile can be achieved by combining low permeable and high permeable coating materials in suitable proportion. An immediate release portion can be added to the extended release system by means of either applying an immediate release layer on top of the extended release core using a coating or compression process or in a multiple unit system such as a capsule containing extended and immediate release beads.

The carrier may be any gel, ointment, lotion, emulsion, cream, foam, mousse, liquid, spray, or aerosol which is capable of delivering the drug to the tissue. In the local drug delivery vehicles described herein, a compounding agent, co-solvent, surfactant, emulsifier, antioxidant, preservative, stabilizer, or diluent may be included in the formulation. A suitable emulsifying agent is needed if the active agent is insoluble in an aqueous environment. A penetration enhancer may be added to enable the active agent to cross the barrier of the stratum corneum. In the preferred embodiment, the carrier is a gel, which is odorless and tasteless and dissolves rapidly, such as a hydroalcoholic gel. Excipients for topical administration may include anti-microbial compounds, e.g. parabens, antioxidants, e.g. sodium ascorbyl acetate and alpha-tocopherol, stabilizers, e.g. sorbitol, or emulsifying agents to produce a stable emulsion with both a hydrophilic and a hydrophobic phase. Suitable carriers or excipients may enhance the physical and chemical stability of the formulation or enhance its aesthetic properties.

Penetration enhancers are frequently used to promote transdermal delivery of drugs across the skin, in particular across the stratum corneum. Some penetration enhancers cause dermal irritation, dermal toxicity and dermal allergies. However, the more commonly used ones include urea, (carbonyldiamide), imidurea, N, N-diethylformamide, N-methyl-2-pyrrolidine, 1-dodecal-azacycloheptane-2-one, calcium thioglycate, 2-pyyrolidine, N,N-diethyl-m-toluamide, oleic acid and its ester derivatives, such as methyl, ethyl, propyl, isopropyl, butyl, vinyl and glycerylmonooleate, sorbitan esters, such as sorbitan monolaurate and sorbitan monooleate, other fatty acid esters such as isopropyl laurate, isopropyl myristate, isopropyl palmitate, diisopropyl adipate, propylene glycol monolaurate, propylene glycol monooleatea and non-ionic detergents such as Brij® 76 (stearyl poly(10 oxyethylene ether), Brij® 78 (stearyl poly (20)oxyethylene ether), Brij® 96 (oleyl poly(10)oxyethylene ether), and Brij® 721 (stearyl poly (21) oxyethylene ether) (ICI Americas Inc. Corp.).

B. Applied to, Immobilized on or Incorporated into Substrates

The peptides may be applied to, absorbed into, or coupled to, a variety of different substrates. Examples of suitable materials include metal, ceramic, polymeric, fibers, and inert materials such as silicon.

Many different medical type devices may be coated with the peptides, such as stents, catheters, implants, fracture fixation devices, and pumps.

Examples of wound dressing that may be coated with, or absorb the antimicrobial peptides include sponges known in the art, including woven and non-woven sponges and those designed specifically for dental or ophthalmic surgeries. See, e.g., U.S. Pat. Nos. 4,098,728; 4,211,227; 4,636,208; 5,180,375; and 6,711,879. The materials can also be absorbed or coated onto paper or polymeric materials used as surgical drapes, disposable diapers, tapes, bandages, and other fibrous materials. The peptides can also be applied directly to, and coupled by ionic, covalent or hydrogen bonding to, or incorporated into, polymeric, metallic, or ceramic substrates, for examples, catheters, tubing, tissue engineering devices, fibrin matrices, heart valves, drug pumps, orthopedic implants, and other devices implanted in or applied to a patient.

C. Coatings, Paints, Dips, Sprays

The peptides can be attached to a substrate using a variety of procedures known in the art, including, but not limited to, chemical vapor deposition and immobilization in thin films. Immobilization of the peptide should minimize concerns regarding toxicity and the development of microbial resistance due to sub-MIC concentrations of the peptide in the body. The covalent attachment of the peptide to the substrate may also extend the effective life of the coating.

Peptides can be immobilized in polymeric materials, such as polymer thin films. The films can be prepared by methods known in the art, such as layer-by-layer construction. The films may be degradable or non-degradable depending on the application. The activity and lifespan of the coatings can be controlled by varying the number of layers, the thickness of the layers, the percent loading of the peptides, and the chemical composition of the thin film layers.

The peptides can also be added to paints and other coatings and filters to prevent mildew, bacterial contamination, and in other applications where it is desirable to provide antimicrobial activity.

The present invention will be further understood by reference to the following non-limiting example.

Example 1

Identification of Grammars for Antimicrobial Peptides

There is mounting evidence that antimicrobial peptides may become effective antibiotic therapies, R. E. W. Hancock, A. Patrzykat, *Current Drug Targets—Infectious Disorders* 2, 70 (2002). Indeed, many AmPs show activity against pathogens that are resistant to traditional antibiotics such as penicillin, tetracycline, and vancomycin, Y. Ge, et al., *Antimicrob Agents Chemother* 43, 782 (1999), E. Tiozzo, G. Rocco, A. Tossi, D. Romeo, *Biochemical and Biophysical Research Communications* 249, 202 (1998), M. B. S. m, et al., *Journal of Medicinal Chemistry* 46, 1567 (2003). In humans, malfunctioning AmPs can lead to severely immunocompromised phenotypes (10, 11) K. Putsep, G. Carlsson, H. G. Boman, M. Andersson, *Lancet* 360, 1144 (2002), H. G. Boman, *Journal of Internal Medicine* 254, 197 (2003). Animal models deficient in AmPs succumb to pathogen challenge, C. L. Wilson, et al., *Science* 286, 113 (1999), whereas transgenic mice expressing human AmPs exhibit a markedly increased resistance to infection, N. H. Salzman, D. Ghosh, K. M. Huttner, Y. Paterson, C. L. Bevins, *Nature* 422, 522 (2003). In addition to their antibiotic uses, AmPs may have other interesting clinical applications: for example they are involved in the immune response of long-term HIV nonprogressors, L. Zhang, et al., *Science* 298, 995 (2002) and may be useful in treating certain cancers, S. Kim, S. S. Kim, Y.-J. Bang, S.-J. Kim, B. J. Lee, *Peptides* 24, 945 (2003), H. M. Ellerby, et al., *Nature Medicine* 5, 1032 (1999), Y. Chen, et al., *Cancer Research* 61, 2434 (2001).

The many disease-relevant behaviors of antimicrobial peptides are understood as a consequence of their ability to broadly distinguish eukaryotic cells from pathogenic invaders. In general, AmPs have a net positive charge and an amphipathic 3-D structure that give the peptides an electrostatic affinity to the out-leaflet of the microbial membrane, A. Giangaspero, L. Sandri, A. Tossi, *European Journal of Biochemistry* 268, 5589 (2201), R. M. Epand, H. J. Vogel, *Biochimica et Biophysica Acta—Biomembrances* 1462, 11 (1999).

Preliminary studies of AmPs indicate that their amphipathic structure gives rise to a modularity among AmP sequences. The repeated usage of sequence modules, for example, the pattern QxEAGxLxKxxK (SEQ ID NO:2) (the "x" means that any amino acid will suffice. The Teiresias pattern discovery tool (see, I. Rigoutsos, A. Floratos, *Bioinformatics* 14, 55 (1998) was employed to elucidate the grammar of AmPs. Given a formal language, Teiresias enumerates right-linear grammars that are maximal in both composition and length.

This process is depicted in FIG. 2B, as discussed above. As shown in FIG. 2A, the grammar space 24 and the functioning AmP space 26, diverge. This represents the understanding that not all sequences that are grammatical will provide a functioning AmP, and not all functioning AmPs will be grammatical, in that they comply with the grammars determined in this process. The depicted divergence indicates that a plurality of candidate AmPs are created through the processes described herein, but each candidate AmP may not ultimately have the same degree of desired biological activity, ranging from barely measurable to levels that are clinically useful, to those that may be acceptable for use in industrial applications where toxicity is not as significant an issue to where toxicity is a concern and must be figured into the effective dosage of the compound for determination of a pharmaceutically acceptable formulation. The peptide design process may optionally filter out from the pool of query sequences those sequences that are known to occur naturally.

The linguistic model focuses the search base to the grammar space but allows a deviation from natural peptide sequences. This allows the system to be employed to design peptides that show little or no significant homology to any naturally occurring sequences, but have the desired function.

Using the set of 526 AmP sequences from University of Nebraska Medical Center Antimicrobial Peptide Database APD, the Teiresias pattern discovery tool was run with the following settings: L=6, W=6, and K=2 (a detailed description of the Teiresias input parameters and associated tools is available elsewhere[i]). The resulting grammar set was masked from the input sequences and the process was repeated using L=7, W=15, K=5 with the following amino acid equivalency groups [[AG], [DE], [FYW], [KR], [ILMV], [QN], [ST]]. (See Rigoutsos and Floratos (1998) for background on pattern discovery, masking, and terminology used in these methods.) Alternatively, other databases may be used such as the AMSdb, A Tossi, Antimicrobial sequences database (AMSDb) (2002), which may be supplemented with about an additional 200 antimicrobial peptides from Swiss-Prot/TrEMBL, A. Bairoch, R. Apweiler, *Nucleic Acids Research* 28, 45 (2002) that were not included in AMSdb.

Teiresias outputs its grammars in regular expression format, using wildcards. To make the grammars more selective, each wildcard in the grammars was de-referenced to a bracketed expression. That is, each wildcard was replaced with the set of amino acids implied by the grammar's offset list. Finally, to allow partial matches as short as 10 amino acids, each grammar was divided into sub-grammars using a sliding-window of size 10, resulting in 1551 grammars of length ten.

By design, these 1551 are sensitive for the AmP sequences from the APD. That is, these sequences from the APD are likely to be matched by the grammars. However, the grammars are not necessarily selective for the APD AmPs. That is, non-AmP sequences may also be matched by the grammars.

To select only those AmP grammars that are both sensitive and selective, we searched each of the grammars against a nearly exhaustive set of all known AmPs. These sequences consisted of approximately 750 AmPs from the AMSdb (http://www.bbcm.univ.trieste.it/~tossi/pag1.htm), which were supplemented with an additional approximately 200 antimicrobial peptides from Swiss-Prot/TrEMBL (Bairoch, et al. Nucleic Acids Res. 28, 45-48 (2000)) that were not included in the AMSdb. In addition, we searched each of the grammars against sequences from Swiss-Prot/TrEMBL that were not AmPs. Using these two searches, we eliminated grammars that were not at least 80% selective for AmPs. That is, at least 80% of the matches for a single grammar had to come from the set of all known AmPs.

The resulting final set of 684 ten amino acid grammars was used to design the unnatural AmPs as described in the text under Methods, Computational design of unnatural AmPs.

Together, the set of 684 grammars may be understood to describe the "language of AmP sequences." In the linguistic model employed, a sequence is a string of amino acids and it is "grammatical" if the sequence conforms to one or more grammars, i.e. it matches at least one regular expression. The semantic interpretation of this sentence is the peptide's function: in this case, antimicrobial activity. For example, the frog AmP brevinin-1E contains the amino acid sequence fragment PKIFCKITRK (SEQ ID NO:4), which matches the grammar P[KAYS][ILN][FGI]C[KPSA][IV][TS][RKC][KR] (SEQ ID NO:5) from the database. The bracketed expression [KAYS] indicates that, at the second position in the grammar, either lysine, alanine, tyrosine, or serine is equally acceptable. Based on this match, one would say that the brevinin-1E fragment is "grammatical".

Example 2

Design of Peptides from Grammars

One can enumerate all or substantially all possible sequences conforming to this grammar. For each grammar sequence one amino acid was chosen for each bracketed position limited to the amino acids within brackets for that corresponding position. For example, in [I/V/L]K[T/E/G/D/K]V[G/A]K[A/E/L/N/H][V/A][G/A]K (SEQ ID NO:3), one may choose one of either I, V or L for the first position and followed a similar procedure for each of the other bracketed positions. In this particular example, one chose one amino acid among each of 3 amino acids in the first position, 5 amino acids in the third position, 2 amino acids in the fifth position, 5 amino acids in the seventh position, 2 amino acids in the eighth position and 2 amino acids in the ninth position. All sequences of ten amino acids in length comprising different combinations of amino acids by multiplying out the number of possible amino acids for each bracketed position were listed, giving us 3×5×2×5×2×2=600 sequences.

This process can be repeated for other grammars in a set of grammars comprising approximately 700 grammars. In this example, one can calculate approximately 3 million peptide sequences comprising ten amino acids conforming to the set of grammars. All or substantially all possible sequences of peptides of twenty amino acids may then be enumerated for each window of ten amino acids. Sequences showing a relatively high degree of similarity to naturally occurring AmP sequences may then be removed. According to this example, one can enumerate approximately 12 million sequences.

These sequences were scored against the grammars and approximately 42 relatively high scoring sequences were selected for chemical synthesis and testing. The number of sequences selected for chemical synthesis and testing was based at least in part on experimental limitations. The designed proteins were chemically synthesized. Once made, the designed proteins and peptides may be experimentally evaluated and tested for structure, function and stability, as required.

FIG. 2B shows an example of a synthesized sequence. Above and below the subsequence are grammars that match the sequence in a tiled arrangement. For each bracketed expression any of the amino acids listed in the bracket will suffice. FIG. 2B depicts a grammar 1 depicted as the sequence:

T[L/G][T/I/P]LL[T/I/S/P][A/T]LL[L/G] (SEQ ID NO:6)

The exemplary grammar derived using the pattern recognition process discussed above includes a sequence of 10 amino acids. The grammar 1 has a number of optional expressions. For example, the second value of sequence may be either L or G. Similarly the third value of the sequence may be T, I or P. The first value of the sequence is T.

Grammar 2, below, is expressed using a similar notation.
[A/F/T]L[I/L]LA[I/V][S/F/A/T][V/A][G/A/D][P/G/S/Q]
(SEQ ID NO:7)

The antimicrobial assays were based on the NCCLS protocol M26-A, and a close variation on that, the method of R W Hancock for Cationic peptides. Cells were grown overnight in Mueller Hinton Broth (MHB) or cation-adjusted MHB. These cells were diluted in fresh MHB to an initial concentration of around $5 \times 10^5$ cfu/ml.

Serial 2 fold dilutions of the antimicrobial were made at 10-fold the desired concentration in sterile water. In the Hancock variation 0.2% BSA and 0.01% Acetic Acid was used rather than water. 11 µl of antimicrobial was added to 100 µl of the innoculum at $5 \times 10^5$ cfu/ml and grown overnight. The minimum inhibitory concentration ("MIC") is the first concentration of peptide that prohibits growth as measured by optical density ("OD") at 24 hours. The minimum bactericidal concentration ("MBC") can be found by performing plate counting on the samples that do not have a measurable OD.

Results

Approximately 42 synthetic AmP sequences were chosen for chemical testing. Table 1 shows the activity of synthetic peptides against microbe strains. The MIC is the first concentration of peptide that prohibits growth as measured by OD at 24 hours. The peptide numbers are serial numbers corresponding to listing of peptides shown in Table 3. The values in the individual cells of Table 1 are concentrations of the peptide at which or greater than which the peptide is active. Specifically, Table 1 shows the activity of synthetic peptides against *Bacillus subtilis* and *Escherichia coli*, as representative gram positive and gram negative bacteria. Table 2 summarizes some of the relevant information in Table 1.

Of 42 designed peptides, approximately 40 were soluble. Of these, 18 had activity against at least one of the bacterial targets at 256 µg/ml or below. 2 of the 40 shuffled, "ungrammatical" sequences display activity. This indicates that the patterns capture more information than helical segregation. Six peptides taken from the middle of non-antimicrobial proteins did not seem to have any measurable activity in these assays using the tested amounts. The quality of the chemically synthesized peptides can be demonstrated by purchasing recombinantly produced versions of five natural AmPs. As shown in Table 1, four of the five had similar activities, with the last being a dilution different. Also, four independently made copies of one peptide had consistent activities against both bacteria.

The activity of the designed peptides was similar to natural AmPs. Eight naturally-occurring AmPs showed a wide range of killing concentration against the target organisms. It should be noted that a number of the positive controls were chosen because they are commercially available and are known to have strong activity. One of the designed peptides, 28, has activity against *Bacillus subtilis* between 12 and 16 µg/ml, which is close to the killing concentrations of the stronger positive controls. Thus, one lead sequence emerged from a screen of approximately 40 designed peptides.

Peptides with gram positive activity are known to show activity against even drug-resistant strains of nosocomial *Staphylococcus aureus* and combat the threat of bioterror agents such as *Bacillus anthracis*, which causes anthrax. Seven designed peptides had gram positive activity against the Smith Diffuse strain of *Staphylococcus aureus* and the Sterne strain of *Bacillus anthracis*. Table 1 shows that all seven peptides had activity against both bacteria, whereas only one of the seven shuffled versions has activity. Two designed peptides have activity against *Bacillus anthracis* equivalent to the activity of Cecropin-melittin hybrid, a strong natural peptide.

TABLE 1

| Peptide number | Sequence/SEQ ID NO: | E. coli | B. cereus |
|---|---|---|---|
| DESIGNATED PEPTIDES | | | |
| 1 | ALFSLASKVVPSVFSMVTKK (9) | + | + |
| 2 | VVFRVASKVFPAVYCTVSKK (10) | 128 | + |
| 5 | FLFGLASKVFPAVYCKVTRK (13) | 64 | 256 |
| 6 | LSAVGKIASKVVPSVIGAFK (14) | + | + |
| 7 | PVIGKLASKVVPSVFSMIKR (15) | + | + |
| 9 | GLMSLVKDIAKLAAKQGAKQ (17) | 256 | + |
| 15 | SALGRVASKVFPAVYCSITK (23) | + | + |
| 22 | LGALFRVASKVFPAVISMVK (30) | 256 | 64 |
| 23 | ALGKLASKVFPAVYCTISRK (31) | 128 | + |
| 24 | GFIGKLASKVVPSVYCKVTG (32) | 128 | + |
| 25 | PVVFSVASKVVPSLISALKR (33) | + | + |
| 28 | FLGVVFKLASKVFPAVFGKV (36) | 64 | 16 |
| 29 | PAVFKIASKVVPSVYCKVSR (37) | 128 | + |
| 30 | GALFGLASKVFPAVFGAFKK (38) | 256 | + |
| 31 | SAVGKLASKVFPAVFSMVTK (39) | + | + |
| 33 | VKDLAKFIAKTVAKQGGCYL (41) | ++ | ++ |
| 34 | GVVGKLASKVVPSVFGSFTK (42) | + | + |
| 35 | LPVVFRVASKVFPALISKLT (43) | + | 256 |
| 36 | SAVGSVASKVVPSLISKVTK (44) | + | + |
| 39 | MKSIAKFIAKTVAKQGAKQG (47) | + | + |
| 42 | LPAVFKLASKVVPSVFGLVK (50) | + | + |
| 43 | SFVFKLASKVVPSVFSALTR (51) | 256 | 256 |
| 44 | SVIGKIASKVVPSVYCAISK (52) | + | + |
| 45 | PVVGRVASKVFPAVIGLVKK (53) | + | + |
| 51 | FLFRVASKVFPALIGKFKKK (59) | 64 | 16 |
| 55 | LSFVGRVASKVVPSLISMIK (63) | 256 | + |
| 56 | SALGRLASKVVPAVIGKVTT (64) | + | + |
| 57 | LGVVGSLASKVVPAVISKVK (65) | + | + |
| 62 | LPAVFKLASKVFPAVYCKAS (70) | 128 | + |

TABLE 1-continued

|  |  | E. coli | B. cereus |
|---|---|---|---|
| 63 | LPVLFKLASKVFPAVFSSLK (71) | 256 | 64 |
| 65 | VVGRVASKVVPSLIGLFTTK (73) | + | + |
| 69 | SVVFGVASKVVPSVIGKVKT (77) | + | + |
| 75 | FLPFVGRIASKVVPSVIGKV (83) | + | + |
| 77 | GKKLAKTIAKEVAKQGAKPA (85) | 64 | + |
| 81 | PFVGRVASKVVPSVYCAITR (89) | Not soluble | |
| 82 | FVGSLASKVVPSVFGAIKTK (90) | + | + |
| 83 | LPVVFKIASKVVPSVISKIT (91) | + | + |
| 84 | GAVFGVASKVVPSVFSAIKK (92) | + | + |
| 85 | FVGGVASKVVPSVYKVSKK (93) | + | + |
| 88 | VVFKLASKVVPSVYCTITKK (96) | 256 | + |
| 96 | GALFSLASKVVPAVIGLIKK (104) | + | 256 |

SHUFFLED PEPTIDES

| 1 | MVVFSVPKFKSTVAKLLSSA (81) | + | + |
|---|---|---|---|
| 2 | TAKVVVFVSFSYVVPKKRAC (40) | + | + |
| 5 | FLPVLVKVFRYSKKTAAGCF (79) | ++ | 64 |
| 6 | GVSSPIVAVKFKGAVASLIK (20) | + | + |
| 7 | SRVPLKSPVKIVGSKVMIFA (76) | + | + |
| 9 | GLKKDALQSIVKKAQLAAMG (22) | + | + |
| 15 | LYSPTCVKAAVSRFIGKVSA (60) | + | + |
| 22 | SVPSVGAVLFFKRAAVMKLI (25) | + | + |
| 23 | KYGPALVIAVKKSCSLTFRA (101) | + | + |
| 24 | GGSTLGVFVKKSKACVIVPY (74) | Not soluble | |
| 25 | KSPFVLVVSSRVAAVIKSLP (21) | + | + |
| 28 | GVSVAGAKKVKVLFVFPFLP (56) | + | + |
| 29 | KVYVVKIAVPCFPKSARSVS (106) | + | + |
| 30 | KVVLFGAAGAKLFKASFFGP (12) | Not enough material | |
| 31 | FMKVLAVFGSVVTSAPKASK (29) | + | + |
| 33 | ALVYAGIKKTAFLKVQKCDG (69) | + | + |
| 34 | SVKPVGSSVVKGTALVKFFG (86) | + | + |
| 35 | KVFIATLVVDDFLLAKPPRV (88) | + | + |
| 36 | STVKVASKLAVVVSPISKGS (61) | + | + |
| 39 | AKKAQKSGAQTIVKIPAKGM (102) | + | + |
| 42 | VVAKKFFVLVKGLAPVLSPS (95) | + | + |
| 43 | ASPTVFRSSVFLSLFVVAKK (87) | + | + |
| 44 | IASAVPCVKGKISKSYISV (67) | + | + |
| 45 | VKRAGKGVAVVPSPLFKIVV (66) | + | + |
| 51 | RKVAPALIKSFVFLPFKFKKG (57) | + | + |
| 55 | SSSIPIKMVLRALVFVKSG (26) | + | + |
| 56 | TLVGVVAKLVATKIGSSPRA (84) | + | + |
| 57 | PKVVGLSIVVVKAKVSSALG (78) | + | + |
| 62 | PSLLYKAKAVFCKPSAVAVF (98) | ++ | ++ |
| 63 | VSVKKVLPFAPLKSLLSFAF (54) | 256 | 256 |
| 65 | FKVVISKPGLSVRVGTALVT (62) | ++ | ++ |
| 69 | VFSVKGGKPSVVIKVVVAST (35) | + | + |
| 75 | SKFPLAGIFSVPGVKRVVVI (45) | + | + |
| 77 | VIAFAKTKEAKAKLKGQAKG (19) | + | + |
| 81 | PAVYKSIVGFSPVARVTVCR (103) | | |
| 82 | KTVPVVLKASIKVSSAGFGF (16) | + | + |
| 83 | KIVKVITVKSISPASLVPVF (97) | ++ | ++ |
| 84 | SVKVAKSVIPSAVFAGGKVF (11) | + | + |
| 85 | KVGKGSYPCSFVKVVAKVSV (99) | + | + |
| 88 | VKTKCSVPAVVYILVKTFKS (100) | + | + |
| 96 | LPVLFSSAIAKVGIKLGAKV (34) | + | + |

NATURAL AMPs

| Peptide | Sequence/SEQ ID NO: | E. coli | B. cereus |
|---|---|---|---|
| Cecropin P1 | SWLSKTAKKLENSAKKRISEGIAIAIQGGPR (8) | 2 | + |
| Cec Mel Hyb | KWKLFKKIGAVL-NH2 (80) | 2 | 8 |
| Magainin 2 | GIGKFLHSAKKFGKAFVGEIMNS (48) | 64 | 256 |
| Melittin | GIGAVLKVLTTGLPALISIKRKRQQ-NH2 (28) | 16 | 8 |
| Parasin | KGRGKQGGKVRAKAKTRSS (75) | + | + |
| Ranalexin | FLGGLIKIVPAMICAVTKKC (24) | 64 | 32 |
| Cec A Mag 2 | KWKLFKKIGIGKFLHSAKKF (68) | 32 | + |
| Pyrrhocoricin | VDKGSYLPRPTPPRPIYNRN (107) | ++ | ++ |

NON-AMP SEQUENCES

| Peptide number | Sequence/SEQ ID NO: | E. coli | B. cereus |
|---|---|---|---|
| 10 | THIHMNARLLIRSPFTDPQL (18) | + | + |
| 19 | RKRKSDVDFEAEFELFEDDD (27) | + | + |
| 38 | AATGTGKTAAFALPVLERLI (46) | + | + |

TABLE 1-continued

|    |                           |   |   |
|----|---------------------------|---|---|
| 50 | PYSLKNGENWLLSEEIIRYP (58) | + | + |
| 74 | KFDPLEGAPMARGIVLEKVG (82) | + | + |
| 86 | HTGRSGPATGHSGHSSTHGS (94) | + | + |

| Peptide number | Sequence/SEQ ID NO: | S. aureus | B. anthracis |
|---|---|---|---|
| DESIGNATED PEPTIDES | | | |
| 28 | FLGVVFKLASKVFPAVFGKV (36) | 8 | 16 |
| 51 | FLFRVASKVFPALIGKFKKK (59) | 16 | 16 |
| 22 | LGALFRVASKVFPAVISMVK (30) | 64 | 64 |
| 63 | LPVLFKLASKVFPAVFSSLK (71) | 128 | 128 |
| 5 | FLFGLASKVFPAVYCKVTRK (13) | 256 | 128 |
| 43 | SFVFKLASKVVPSVFSALTR (51) | 256 | 128 |
| 35 | LPVVFRVASKVFPALISKLT (43) | 256 | 128 |
| SHUFFLED PEPTIDES | | | |
| 28 | GVSVAGAKKVKVLFVFPPLF (56) | + | + |
| 51 | RKVAPALIKSFVFLFKFKKG (57) | 128 | 256 |
| 22 | SVPSVGAVLFFKRAAVMKLI (25) | + | + |
| 63 | VSVKKVLPFAPLKSLLSFAF (54) | + | + |
| 5 | FLPVLVKVFRYSKKTAAGCF (79) | + | + |
| 43 | ASPTVFRSSVFLSLFVVAKK (87) | + | + |
| 35 | KVFIATLVVSSFLLAKPPRV (88) | + | + |

NATURAL AMPs

| Peptide Number | Sequence/SEQ ID NO: | S. aureus | B. anthracis |
|---|---|---|---|
| Cec Mel Hyb | KWKLFKKIGAVLKVL-NH2 (80) | 4 | 16 |
| NON-AMP SEQUENCES | | | |
| 10 | THIHMNARLLIRSPFTDPQL (18) | + | + |

+ = MIC greater than 256 ug/mL
++ = MIC greater than 128 ug/mL, not sufficiently soluble to test as 256 ug/mL

TABLE 2

MICs of peptides against bacterial targets

| Class | E. coli (gram negative) | | B. cereus (gram positive) | | Either E. coli or B. cereus MIC ≤256 ug/ml |
|---|---|---|---|---|---|
| | MIC ≤256 ug/ml | MIC ≤64 ug/ml | MIC ≤256 ug/ml | MIC ≤64 ug/ml | |
| Designed | 16/40 | 4/40 | 8/40 | 4/40 | 18/40 |
| Shuffled | 1/38 | 0/38 | 2/38 | 1/38 | 2/38 |
| Natural AmPs | 6/8 | 6/8 | 4/8 | 3/8 | 6/8 |

TABLE 3

| 0 | SWLSKTAKKLENSAKKRISEGIAIAIQGGPR | (SEQ ID NO:8) |
|---|---|---|
| 1 | ALFSLASKVVPSVFSMVTKK | (SEQ ID NO:9) |
| 2 | VVFRVASKVFPAVYCTVSKK | (SEQ ID NO:10) |
| 3 | SVKVAKSVIPSAVFAGGKVF | (SEQ ID NO:11) |
| 4 | KVVLFGAAGAKLFKASFFGP | (SEQ ID NO:12) |
| 5 | FLFGLASKVFPAVYCKVTRK | (SEQ ID NO:13) |
| 6 | LSAVGKIASKVVPSVIGAFK | (SEQ ID NO:14) |
| 7 | PVIGKLASKVVPSVFSMIKR | (SEQ ID NO:15) |
| 8 | KTVPVVLKASIKVSSAGFGF | (SEQ ID NO:16) |
| 9 | GLMSLVKDIAKLAAKQGAKQ | (SEQ ID NO:17) |
| 10 | THIHMNARLLIRSPFTDPQL | (SEQ ID NO:18) |
| 11 | VIAFAKTKEAKAKLKGQAKG | (SEQ ID NO.19) |
| 12 | GVSSPIVAVKFKGAVASLIK | (SEQ ID NO:20) |
| 13 | KSPFVLVVSSRVAAVIKSLP | (SEQ ID NO:21) |
| 14 | GLKKDALQSIVKKAQLAAMG | (SEQ ID NO:22) |

TABLE 3-continued

| | | |
|---|---|---|
| 15 | SALGRVASKVFPAVYCSITK | (SEQ ID NO:23) |
| 16 | FLGGLIKIVPAMICAVTKKC | (SEQ ID NO:24) |
| 17 | SVPSVGAVLFFKRAAVMKLI | (SEQ ID NO:25) |
| 18 | SSSIPIKMVLVRALVEVKSG | (SEQ ID NO:26) |
| 19 | RKRKSDVDFEAEFELFEDDD | (SEQ ID NO:27) |
| 20 | GIGAVLKVLTTGLPALISWIKRKRQQ-NH2 | (SEQ ID NO:28) |
| 21 | FMKVLAVFGSVVTSAPKASK | (SEQ ID NO:29) |
| 22 | LGALFRVASKVFPAVISMVK | (SEQ ID NO:30) |
| 23 | ALGKLASKVFPAVYCTISRK | (SEQ ID NO:31) |
| 24 | GFIGKLASKVVPSVYCKVTG | (SEQ ID NO:32) |
| 25 | PVVFSVASKVVPSLISALKR | (SEQ ID NO:33) |
| 26 | LPVLFSSAIAKVGIKLGAKV | (SEQ ID NO:34) |
| 27 | VFSVKGGKPSVVIKVVVAST | (SEQ ID NO:35) |
| 28 | FLGVVFKLASKVFPAVFGKV | (SEQ ID NO:36) |
| 29 | PAVFKIASKVVPSVYCKVSR | (SEQ ID NO:37) |
| 30 | GALFGLASKVFPAVFGAFKK | (SEQ ID NO:38) |
| 31 | SAVGKLASKVFPAVFSMVTK | (SEQ ID NO:39) |
| 32 | TAKVVVFVSFSYVVPKKRAC | (SEQ ID NO:40) |
| 33 | VKDLAKFIAKTVAKQGGCYL | (SEQ ID NO:41) |
| 34 | GVVGKLASKVVPSVFGSFTK | (SEQ ID NO:42) |
| 35 | LPVVFRVASKVFPALISKLT | (SEQ ID NO:43) |
| 36 | SAVGSVASKVVPSLISKVTK | (SEQ ID NO:44) |
| 37 | SKFPLAGIFSVPGVKRVVVI | (SEQ ID NO:45) |
| 38 | AATGTGKTAAFALPVLERLI | (SEQ ID NO:46) |
| 39 | MKSIAKFIAKTVAKQGAKQG | (SEQ ID NO:47) |
| 40 | GIGKFLHSAKKFGKAFVGEIMNS | (SEQ ID NO:48) |
| 41 | ICIFCCGCCHRSKCGMCCKT | (SEQ ID NO:49) |
| 42 | LPAVFKLASKVVPSVFGLVK | (SEQ ID NO:50) |
| 43 | SFVFKLASKVVPSVFSALTR | (SEQ ID NO:51) |
| 44 | SVIGKIASKVVPSVYCAISK | (SEQ ID NO:52) |
| 45 | PVVGRVASKVFPAVIGLVKK | (SEQ ID NO:53) |
| 46 | VSVKKVLPFAPLKSLLSFAF | (SEQ ID NO:54) |
| 47 | NVPGVEYYEIETGLGKFKYA | (SEQ ID NO:55) |
| 48 | GVSVAGAKKVKVLFVFPFLF | (SEQ ID NO:56) |
| 49 | RKVAPALIKSFVFLFKFKKG | (SEQ ID NO:57) |
| 50 | PYSLKNGENWLLSEEIIRYP | (SEQ ID NO:58) |
| 51 | FLFRVASKVFPALIGKFKKK | (SEQ ID NO:59) |
| 52 | LYSPTCVKAAVSRFIGKVSA | (SEQ ID NO:60) |
| 53 | STVKVASKLAVVSPISKGS | (SEQ ID NO:61) |
| 54 | FKVVISKPGLSVRVGTALVT | (SEQ ID NO:62) |
| 55 | LSFVGRVASKVVPSLISMIK | (SEQ ID NO:63) |
| 56 | SALGRLASKVVPAVIGKVTT | (SEQ ID NO:64) |
| 57 | LGVVGSLASKVVPAVISKVK | (SEQ ID NO:65) |
| 58 | VKRAGKGVAVVPSPLFKIVV | (SEQ ID NO:66) |
| 59 | IASAVPVCVKGKISKSYISV | (SEQ ID NO:67) |
| 60 | KWKLFKKIGIGKFLHSAKKF | (SEQ ID NO:68) |
| 61 | ALVYAGIKKTAFLKVQKCDG | (SEQ ID NO:69) |
| 62 | LPAVFKLASKVFPAVYCKAS | (SEQ ID NO:70) |
| 63 | LPVLFKLASKVFPAVFSSLK | (SEQ ID NO:71) |
| 64 | SIHIGPGRAFYATGNIIGDI | (SEQ ID NO:72) |
| 65 | VVGRVASKVVPSLIGLFTTK | (SEQ ID NO:73) |
| 66 | GGSTLGVFVKKSKACVIVPY | (SEQ ID NO:74) |
| 67 | KGRGKQGGKVRAKAKTRSS | (SEQ ID NO:75) |
| 68 | SRVPLKSPVKIVGSKVMIFA | (SEQ ID NO:76) |
| 69 | SVVFGVASKVVPSVIGKVKT | (SEQ ID NO:77) |
| 70 | PKVVGLSIVVVKAKVSSALG | (SEQ ID NO:78) |
| 71 | FLPVLVKVFRYSKKTAAGCF | (SEQ ID NO:79) |
| 72 | KWKLFKKIGAVLKVL-NH2 | (SEQ ID NO:80) |
| 73 | MVVFSVPKFKSTVAKLLSSA | (SEQ ID NO:81) |
| 74 | KFDPLEGAPMARGIVLEKVG | (SEQ ID NO:82) |
| 75 | FLPFVGRIASKVVPSVIGKV | (SEQ ID NO:83) |
| 76 | TLVGVVAKLVATKIGSSPRA | (SEQ ID NO:84) |
| 77 | GKKLAKTIAKEVAKQGAKFA | (SEQ ID NO:85) |
| 78 | SVKPVGSSVVKGTALVKFFG | (SEQ ID NO:86) |
| 79 | ASPTVFRSSVFLSLFVVAKK | (SEQ ID NO:87) |
| 80 | KVFIATLVVSSFLLAKPPRV | (SEQ ID NO:88) |
| 81 | PFVGRVASKVVPSVYCAITR | (SEQ ID NO:89) |
| 82 | FVGSLASKVVPSVFGAIKTK | (SEQ ID NO:90) |
| 83 | LPVVFKIASKVVPSVISKIT | (SEQ ID NO:91) |
| 84 | GAVFGVASKVVPSVFSAIKK | (SEQ ID NO:92) |
| 85 | FVGGVASKVVPSVYCKVSKK | (SEQ ID NO:93) |
| 86 | HTGRSGPATGHSGHSSTHGS | (SEQ ID NO:94) |
| 87 | VVAKKFFVLVKGLAPVLSPS | (SEQ ID NO:95) |
| 88 | VVFKLASKVVPSVYCTITKK | (SEQ ID NO:96) |
| 89 | KIVKVITVKSISPASLVPVF | (SEQ ID NO:97) |
| 90 | PSLLYKAKAVFCKPSAVAVF | (SEQ ID NO:98) |
| 91 | KVGKGSYPCSFVKVVAKVSV | (SEQ ID NO:99) |
| 92 | VKTKCSVPAVVYILVKTFKS | (SEQ ID NO:100) |
| 93 | KYGPALVIAVKKSCSLTFRA | (SEQ ID NO:101) |

TABLE 3-continued

| 94 | AKKAQKSGAQTIVKIFAKGM | (SEQ ID NO:102) |
| --- | --- | --- |
| 95 | PAVYKSIVGFSPVARVTVCR | (SEQ ID NO:103) |
| 96 | GALFSLASKVVPAVIGLIKK | (SEQ ID NO:104) |
| 97 | AVLFVMFLSLIGLLAIAGIR | (SEQ ID NO:105) |
| 98 | KVYVVKIAVPCFPKSARSVS | (SEQ ID NO:106) |
| 99 | VDKGSYLPRPTPPRPIYNRN | (SEQ ID NO:107) |

Example 3

Design and Synthesis of Variants of Synthetic AmPs; Drug Discovery, Using the Peptides Designed in Example 2

Previous approaches to the design of synthetic AmPs have produced peptides that are either closely related to naturally occurring peptides, or that are composed of only a handful of amino acids, for example, poly-lysine peptides, E. Tiozzo, G. Rocco, A. Tossi, D. Romeo, *Biochemical and Biophysical Research Communications* 249, 202 (1998), A. Tossi, L. Sandri, A. Giangaspero, *Biopolymers* 55, 4 (2000). In contrast, these synthetic AmPs, by design, have an amino acid distribution similar to that of natural proteins or peptides and they populate a region of sequence space that is not occupied naturally occurring AmPs. This establishes that the linguistic approach is a means to rationally expand the natural sequence space without using structure-activity information or complex folding simulations. Instead, the process relies upon the ability of sequence grammars to capture the underlying functions of the peptides. These grammars help to establish bounds on the set of synthetic sequences that are likely to have antimicrobial activity.

The described linguistic design method is valuable as a first module of a two-stage drug discovery process. Diverse leads generated by these algorithms and processes can be modified and optimized through relatively exhaustive or rational mutations. To demonstrate this process, 44 variants of peptide #28 (Table 1) were made. Mutations were selected to increase positive charge, increase hydrophobicity, substantially remove an interior proline residue, and improve segregation of positive and hydrophobic residues based at least in part on a helical projection. This was done using the PEPWHEEL program from "The European Molecular Biology Open Software Suit" OR EMBOSS. (*EMBOSS: The European Molecular Biology Open Software Suite* (2000) Rice, P. Longden, I. and Bleasby, A. Trends in Genetics 16, (6) pp 276-277).

Improved activities resulted from the optimization, with one peptide having activity of 16 ug/ml against *Escherichia coli* and 8 µg/ml against *Bacillus cereus*. One structure function relationship includes removing proline tends to improve activity against *Bacillus cereus*.

The hemolytic concentration at which the peptides lyse 50% of human red blood cells ($HC_{50}$) was also measured, as a test of peptide toxicity. While one of the two peptides of interest, #28, had an $HC_{50}$ of 42 µg/ml, the other, #51, had an $HC_{50}$ greater than 512 µg/ml. Hemolytic activity may not be directly correlated with antimicrobial activity. The processes may be used to identify revised linguistic patterns that code for antimicrobial activity without toxicity as one collects a database of hemolytic activity.

The uniqueness of the designed peptides was also characterized. Some degree of homology with natural AmPs seems to be inherent in the linguistic algorithm because the regular expressions are based at least in part on native sequences. Peptide #28, for example, had patterns related to about 11 natural AmPs including brevinin, temporin, and ponericin. The homology of the peptides was assessed by performing Smith-Waterman alignment against all natural AmPs. Two peptides of interest, #51 and #28, are shown to have 50% and 60% sequence identity with the nearest natural AmP, respectively.

Those skilled in the art will know or be able to ascertain using no more than routine experimentation, many equivalents to the embodiments and practices described herein. Accordingly, it will be understood that the invention is not to be limited to the embodiments disclosed herein, but is to be understood from the following claims, which are to be interpreted as broadly as allowed under the law.

We claim:

1. A method of identifying antimicrobial peptides comprising:
    (a) providing a database of known antimicrobial peptides,
    (b) defining a set of integer parameters comprising L, W and K,
    wherein L is the minimum number of characters that may define a pattern,
    wherein L/W is the minimum density of non-wild card characters over a window of W characters, and
    wherein K is the minimum number of times a pattern occurs in the database,
    (c) screening the database with an algorithm that discovers all grammars in the database of antimicrobial peptides by applying integer parameters L=6, W=6, and K=2,
    (d) masking the resulting grammars from the input sequences,
    (e) repeating the algorithm with L=7, W=15, and K=5 with the amino acid equivalency group [[AG], [DE], [FYW], [KR], [ILMV], [QN], [ST]],
    (f) dividing all grammars to sliding windows of ten amino acids,
    (g) filtering grammars for selectivity by eliminating grammars that are not 80% selective for antimicrobial peptides in a database of known antimicrobial peptides from AMSdb and known antimicrobial peptides from Swiss-Prot/TrEMBL,
    (h) enumerating all 20 amino acid sequences which are matched over every sliding window of 10 amino acids by at least one grammar,
    (i) scoring the enumerated sequences against the grammars of step (g), and selecting relatively high scoring sequences for synthesizing and testing, and
    (j) testing the synthesized sequences for antimicrobial activity.

2. The method of claim 1 wherein the database is the set of 526 AmP sequences present in the 2002 University of Nebraska Medical Center Antimicrobial Peptide Database APD.

3. The method of claim 1 wherein the database is the set of 526 AmP sequences present in the 2002 University of Nebraska Medical Center Antimicrobial Peptide Database APD, AMSdb, supplemented with about an additional 200 antimicrobial peptides from Swiss-Prot/TrLMBL, that were not included in AMSdb, for use with the selectivity filter.

* * * * *